(12) United States Patent
Contag et al.

(10) Patent No.: US 6,638,752 B2
(45) Date of Patent: Oct. 28, 2003

(54) BIODETECTORS TARGETED TO SPECIFIC LIGANDS

(75) Inventors: Pamela R. Contag, San Jose, CA (US); Christopher H. Contag, San Jose, CA (US); David A. Benaron, Portolla Valley, CA (US)

(73) Assignee: Xenogen Corporation, Alameda, CA (US)

( * ) Notice: Subject to any disclaimer, the term of this patent is extended or adjusted under 35 U.S.C. 154(b) by 0 days.

(21) Appl. No.: 09/183,566

(22) Filed: Oct. 30, 1998

(65) Prior Publication Data

US 2002/0086424 A1 Jul. 4, 2002

Related U.S. Application Data

(63) Continuation-in-part of application No. 08/844,336, filed on Apr. 18, 1997.
(60) Provisional application No. 60/015,633, filed on Apr. 19, 1996.

(51) Int. Cl.$^7$ ................................................ C12N 1/21
(52) U.S. Cl. ........................ 435/252.3; 435/8; 435/69.1; 435/69.6; 435/69.7
(58) Field of Search ............................. 435/69.7, 69.6, 435/252.3, 69.1, 8

(56) References Cited

U.S. PATENT DOCUMENTS

| | | |
|---|---|---|
| 4,745,181 A | 5/1988 | Law et al. |
| 5,281,539 A | 1/1994 | Schramm |
| 5,283,179 A | 2/1994 | Wood |
| 5,348,867 A | 9/1994 | Georgiou et al. |
| 5,418,132 A | 5/1995 | Olivo |
| 5,466,575 A | 11/1995 | Cozzette et al. |
| 5,591,604 A | 1/1997 | Fuchs et al. |
| 5,612,184 A | 3/1997 | Rosson |
| 5,622,868 A | 4/1997 | Clarke et al. |
| 5,650,135 A | 7/1997 | Contag et al. |

FOREIGN PATENT DOCUMENTS

| | | |
|---|---|---|
| EP | 0 730 868 A1 | 2/1996 |
| WO | WO 86/01806 | 3/1986 |
| WO | WO 86/01850 | 3/1986 |
| WO | WO 91/01305 | 2/1991 |
| WO | WO 97/08553 | 3/1997 |

OTHER PUBLICATIONS

Allgood, et al. 1997 "Chimeric receptors as gene switches." *Current Opinion in Biotechnology* 8:474–479.
Askin, 1995 "Bacterial and Fungal Infections in the Neonate." *Journal of Obstetricm, Gynecologic, Neonatal Nurses* 24(7):635–643.
Banaron, et al. 1993 "Medical Optical Tomography: Functional Imaging and Monitoring." *SPIE Optical Engineering Press*: 3–9.
Benaron, et al. 1993 "Optical Time–of–Flight and Absorbance Imaging of Biologic Media." *Science* 259:1463–1466.
Benaron, et al. 1994 "Resolution of Near Infrared Time–of–Flight Brain Oxygenation Imagining." *Advances in Experimental Medicine and Biology* 345:609–617.
Ben–Israel, et al. 1998 "Identification and Quantification of Toxic Chemicals by Use of *Escherichia coli* Carrying lux Genes Fuse to Stress Promoters." *Applied and Environmental Microbiology* 64(11):4346–4352.
Billard, et al. 1998 "Bioluminescence–Based Arrays for Detection and Characterization and Bacteria and Chemicals in Clinical Laboratories." *Clinical Biochemistry* 31:1–14.
Blom, et al. 1993 "A Baculovirus–Expressed Fusion Protein Containing the Antibody–Binding Domain of Protein A and Insect Luciferase." *BioTechniques* 14(5):800–809.
Blum, et al. 1989 "Design of luminescence photobiosensors." *Journal of Bioluminescence and Chemilumenscence* 4:543–550.
Borrebaeck, et al. 1992 "Kinetic analysis of Recombinant Antibody–Antigen Interactions: Relation Between Structural Domains and Antigen Binding." *Biotechnology* 10(60):697–698.
Braiser, et al. 1992 "Luciferase Reporter Gene Assay in Mammalian Cells." *Meth. In Enzymology* 216:386–396.
Brennan, et al. 1995 "A molecular sensor system based on genetically engineered alkaline phosphatase." *Proc. Natl. Acad. Sci. USA* 92:5783–5787.
Cai, et al., 1997 "Use of a luminescent bacterial biosensor for biomonitoring and characterization of arsenic toxicity of chromated copper arsenate (CCA)" *Biodegradation* 8:105–111.
Candido, et al. 1996 "Transgenic Caenorhabditis elegans strains as biosensors." *Trends in Biotechnology* 14:125–129.
Casadei, et al. 1990 "Expression and secretion of eequorin as a chimeric antibody by means of a mammalian expression vector." *Proc. Natl. Acad. Sci. USA* 87:2047–2051.
Clark, et al. 1994 "Unsuspected Primary Human Immunodeficiency Virus Type Type 1 Infection in Seronegative Emergency Department Patients." *The Journal of Infectious Diseases* 170:194–197.
Collet, et al. 1992 "A binary plasmid system for shuffling combinatorial antibody libraries." *Proc. Natl. Acad. Sci. USA* 89:10026–10030.
Contag, et al. 1995 "Photonic detection of bacterial pathogens in living hosts." *Molecular Microbiology* 18(4):593–603.

(List continued on next page.)

*Primary Examiner*—Lynette R. F. Smith
*Assistant Examiner*—Robert A. Zeman
(74) *Attorney, Agent, or Firm*—Robins & Pasternak LLP

(57) ABSTRACT

The present invention relates to biodetectors for detecting and quantifying molecules in liquid, gas, or matrices. More specifically, the present invention relates to biodetectors comprising a molecular switching mechanism to express a reporter gene upon interaction with target substances. The invention further relates to methods using such biodetectors for detecting and quantifying selected substances with high specificity and high sensitivity.

18 Claims, 6 Drawing Sheets

OTHER PUBLICATIONS

Contag, et al. 1997 "Visualizing Gene Expression in Living Mammals Using a Bioluminescent Reporter." *Photochemistry and Photobiology* 66(4):523–531.

Danilov, et al. 1989 "Bacterial Luciferase as a Biosensor of Biologically Active Compounds." *Biotechnology* 11:39–78.

DiLella, et al. 1988 "Utility of firefly luciferase as a receptor gene for promoter activity in transgenic mice." *Nucleic Acids Research* 16(9):4159.

Enberg, et al. 1994 "Growth hormone (GM) regulation of a rat protease inhibitor fusion gene in cells transfected with GH receptor cDNA." *Journal of Molecular Endocriology* 12:39–46.

Frackman, et al. 1990 "Cloning, Organization, and Expressin of the Bioluminescence Genes of Xenorhabdus luminescens." *Journal of Bacteriology* 172(10):5767–5773.

Francisco, et al. 1994 The Expression of Recombinant Proteins on the External Surface of *Escherichia coli*. *Ann. NY. Acad. Sci* 745:372–383.

Fuchs, et al. 1991 "Targeting Recombinant Antibodies to the Surface of *Escherichia Coli*. Fusion to a peptiodoglycan Associated Lipoprotein." *Biotechnology* 9:1369–1372.

Georgiou, et al. 1993 "Practical applications of engineering Gram–negative bacterial cell surfaces." *Tibtech* 11:6–10.

Georgiou, et al. 1997 "Display of heterologous proteins on the surface of microorganisms: From the screening of combinatorial libraries to live recombinant vaccines." *Nature biotechnology* 15:29–34.

Griffiths, et al. 1998 Strategies for selection of antibodies by phage display. *Current Opinion in biotechnology* 9:102–108.

Guzzo, et al. 1992 "Characterization of the effects of aluminum of luciferase biosensors for the detection of ecotoxicity." *Toxicology Letters*, 64/65:687–693.

Hannibal, et al. 1994 "Multiple cis–acting elements in the human immunodeficiency virus type 2 enhancer mediate the response to T–cell receptor stimulation by antigen in a T–cell hybridoma line." *Blood* 83(7):1839–1846.

Harlow, et al. 1988 "Antibodies. A Laboratory Manual." *Cold Spring Harbor Laboratory Press*.

Hasemann, et al. 1989 "Immunoglobulins: Structure and Function", *In Fundamental Immunology* $2^{nd}$ (Ed.) W.E. Paul:209–233.

Heitzer, et al. 1994 "Optical Biosensor for Environmental On–Line Monitoring of Naphthalene and Salicylate Bioavailability with an Immobilized Bioluminescent Catabolic Reporter Bacterium." *Applied an Environmental Microbiology* 60(5):1487–1494.

Hickey, et al. 1996 "Luciferase in Vivo Expression Technology: Use of Recombinant Mycobacterial Reporter Strains to Evaluate Antimycobacterial Activity in Mice." *Antimicrobial Agents and Chemotherapy* 40(2):400–407.

Hoogenboom, et al. 1991 "Multi–subunit proteins on the surface of filamentous phage: methodologies for displaying antibody (Fab) heavy and light chains." *Nucleic Acids Research* 19(15):4133–4137.

Hooper, et al. 1994 "Low–Light Imaging Technology in the Life Sciences." *Journal of Bioluminescence and Chemiluminescence* 9:113–122.

Horan, et al. 1990 "Fluorescent Cell Labeling for in vivo and in vitro cell Tracking." *Methods in Cell Biology* 33:469–490.

Huse, et al. 1989 "Generation of a Large Combinatorial Library of the Immunoglobulin Repertorie in Phage Lambda." *Science* 246:1275–1281.

Israel, 1991 "Bioluminescence assay for gene expression by continuously growing mammalian cells: application for detection of human immunodeficiency virus type 1 (HIV–1)." *Gene* 104:139–145.

Jassim, et al. 1990 "In vivo Bioluminescence: A Cellular Reporter for Research and Industry." *Journal of Bioluminscence and Chemiluminescence* 5:115–122.

Karube, et al. 1994 "Immoblizlied cells used for detection and analysis." *Currn. Opin. Biotechnol.* 5(10):54–59.

Kasahara, et al. 1991 "Molecular Analysis of the Salmonella typhimurium phoNGene, Which Encodes Nonspecific Acid Phosphatase." *Journal of Bacteriology* 173(2):6760–6765.

Kasahara, et al. 1992 "Molecular Analysis of the Escherichia coli phoP–phoQ operon." *Journal of Bacteriology* 174(2):492–498.

Kobatake, et al., 1995 "Biosensing of benzene derivatives in the environment by luminescent *Escherichia coli*" *Biosensors & Bioelectronics* 10:601–605.

Kohl, et al. 1990 "Engineered gene for *Escherichia coli* alkaline Phosphatase for the construction of transnational fusions." *Nucleic Acids Res.* 18:1069.

Kohl, et al. 1991 "Cloning and Expression of an HIV–1 Specific Single–Chain F, Region Fused to *Escherichia coli* Alkaline Phosphatase." *Ann NY Acad Sci.* 646:106–114.

Korpela, et al. 1989 "Stable–light emitting *Escherichia coli* as a Biosensor." *Journal of Bioluminescence and Chemiluminescence* 4(1):551–554.

Kovas, et al. 1991 "Firefly luciferase as a marker for herpesvirus (pseudorabies virus) replication in vitro and in vivo." *J. Gen. Virol.* 72:2999–3008.

Kricka, et al. 1991 "Chemiluminescent and Bioluminescent Techniques." *Clinical Chemistry* 37(9):1472–1481.

Kubo, et al. 1991 "Whole–Organism Based Biosensors and Microbiosensors." *Advances in Biosensors* 1:1–32.

Little, et al. 1993 Bacterial surface presentation of proteins and pepetides: an alternative to phage technology? *Tibtech* 11:3–5.

Little, et al. 1994 "Thermostability of bacterial luciferase expressed in different microbes." *J. Appl. Bacteriology* 77:149–54.

Mayer, et al. 1994 Luminescent Labels–More than Just an Alternative to Radioisotopes?. *Angewandte Chemie International Editiojn* 33:1044.

McCafferty, et al. 1990 "Phage antibodies: filamentous phage displaying antibody variable domains." *Nature* 348:552–554.

Meighen, 1993 "Bacterial bioluminescence: organization, regulation, and application of the lux genes." *The FASEB Journal* 7:1016–1022.

Miller, et al., 1989 "A two–component regulatory system (phoP phoQ) controls *Salmonella typhimurium* virulence." *Proc. Natl. Acad. Sci USA* 86:5054–5058.

Miller, 1991 "PhoP/PhoQ: macrophage–specific modulators of Salmonella virulence?" *Molecular Microbiology* 5(9):2073–2076.

Mueller–Klieser, et al. 1993 "Geographical mapping of metabolites in biological tissue with quantitative bioluminescence and single photon imaging." *Histochemical Journal* 25:407–420.

Orum, et al. 1993 "Efficient method for constructing comprehensive murine Fab antibody libraries displayed on phage." *Nucleic Acids Research* 21(19):4491–4498.

Ottenmann, et al. 1993 "Converting a transmembrane receptor to a soluble receptor: Recognition domain to effector domain signaling after excision of the transmembrane domain." *Proc. Natl. Acad. Sci. USA* 94:11201–11204.

Parkinson, 1993 "Signal Transduction Schemes of Bacteria." *Cell* 73:857–871.

Phadke, 1992 "Biosensors and enzyme immobilized electrodes." *BioSystems* 27(40):203–206.

Piatak, et al. 1993 "Determination of plasma viral load in HIV–1 infection by quantitative competitive polymerase chain reaction." *Aids Supplemental*, 7(supp 2):S65–S71.

Prest, et al. 1997 "The construction and application of a lux–based nitrate biosensor" *Letters in Applied Microbiology* 24:355–360.

Ramanathan, et al. 1997 "Bacterial biosensors for monitoring toxic metals." *Trends Biotechnol* 15:500–506.

Ronald, et al. 1990 "Construction of broad–host–range vectors for the selection of divergent promoters." *Gene* 90:145–148.

Rupani, et al. 1996 "Characterization of the Stress Response of a Bioluminescent Biological Sensor in Batch and Continuous Cultures." *Biotechnol. Prog.* 12:387–392.

Sedlack, et al 1995 "Bioluminescent Technology for Reagents, Diagnostics and Toxicology." Genetic Engineering News *Genetic Engineering News* 8 (Sep. 15, 1995).

Selifonova, et al. 1993 "Bioluminescent Sensors for Detection of Bioavailable Hg(II) in the Environment" *Applied and Environmental Microbiology* 59(9):3083–3090.

Soncini, et al. 1995 "Transcriptional Autoregulation of the Salmonella typhimurium phoPQ operon." *Journal of Bacteriology* 177(5):4364–4371.

Soncini, et al. 1996 "Molecular Basis of the Magnesium Deprivation Response in Salmonella typhimurium Identification of PhoP–Regulated Genes." *Journal of Bacteriology* 178(17):5092–5099.

Stahl, et al. 1997 "Bacterial surface display: trends and progress." *Tibtech* 15:185–192.

Sticher, et al., 1997 "Development and Characterization of a Whole–Cell Bioluminescent Sensor for Bioavailable Middle–Chain Alkanes in Contaminates Groundwater Samples" *Applied and Environmental Microbiology* 63:4053–4060.

Swift, et al. 1994 "Gram–negative bacterial communication by N–acyl homoserine lactoines: a universal language?" *Trends in Microbiology* 193:2(6):193–198.

Szittner, et al. 1990 "Nucleotide Sequence, Expression, and Properties of Luciferase Coded by lux Genes from a Terrestrial Bacterium." *Journal of Biological Chemistry* 265:16581–16587.

Tatsu, 1990 "Homogenous chemiluminescent Immunoassay Based on Complement–Mediated Hemolysis of Red Blood Cells." *Analytical Chemistry* 62:2103–2106.

Ulitzur, 1997 "Review Paper: Established Technologies and New Approaches in Applying Luminous Bacteria of Analytical Purposes." *J. Biolumin Chemilumin* 12:179–192.

Van Dyk, et al. 1994 "Rapid and sensitive pollutant detection by induction of heat shock gene–bioluminescent gene fusions." *Applied and Environment Mirobiology* 60(50):1414–1420.

Vescovi–Garcia, et al. 1996 "MG2+ as an Extracellular Signal: Environmental Regulation of Salmonella Virulence." *Cell* 84:165–174.

von Bally, et al. 1981 "Optics in Biomedical Sciences." *Proceedings of the International Conference*, Berline, New York: Springer–Verlag.

Weiss, et al. 1994 Application of an alkaline phosphatase fusion protein system suitable for efficient screening and production of Fab–enzyme conjugates in *Escherichia coli*. *Journal of Biotechnology* 33:43–53.

Willardson, et al. 1998 "Development and Testing of a Bacterial Biosensor for Toluene–Based Environmental Contaminants." *Applied and Environmental Microbiology* 64(3):1006–1012.

Wood, et al. 1996 "Transduction in microbial biosensors using multiplexed bioluminescence." *Biosensors & Bioelectronics* 11(3):207–214.

Xi, 1991 "Cloning and Nucleotide Sequences of lux Genes and Characterizatin of Luciferase of Xenorhabdus luminescens from a Human Wound." *Journal of Bacteriology* 173:1399–1405.

Wilmes–Riesenberg, et al. 1992 "TnphoA and TnphoA' elements for making and switching fusions for study of transcription, translation, and cell surface localization." *J. Bacteriol* 174:4558–75.

Zhang, et al. 1994 "Luciferase activity as a market of tumor burden and as an indicator of tumor response to antineoplastic therapy in vio." *Clin. Exp. Metastasis* 12(12):87–92.

Zipkin, 1997 "Xenogen: Peering into hidden regions." *Biocentury* (The Bernstein Report) Dec. 8, 1997.

Zlokarnik, et al. 1998 "Quantitation of Transcription and Clonal Selection of Single Living Cells with B–Lactamase as Reporter." *Science* 279:84–88.

A. IN THE PRESENCE OF LIGAND ($Amp^r$, $Kan^r$, $Chl^s$ AND BIOLUMINESCENT).

B. IN THE PRESENCE OF LIGAND ($Amp^r$, $Kan^r$, $Chl^s$ AND *NOT* BIOLUMINESCENT).

BIODETECTORS TARGETED TO SPECIFIC LIGANDS

This application is a continuation-in-part of co-owned, co-pending U.S. patent application Ser. No. 08/844,336, filed Apr. 18, 1997, which claims the benefit of U.S. Provisional Application No. 60/015,633, filed Apr. 19, 1996.

I. FIELD OF THE INVENTION

The present invention relates to biodetectors for detecting and quantifying molecules in liquid, gas, or on solid matrices. More specifically, the present invention relates to biodetectors comprising a molecular switching mechanism to express a reporter gene upon interaction with target substances. The invention further relates to methods using such biodetectors for detecting and quantifying selected substances with high specificity and sensitivity.

II. BACKGROUND OF THE INVENTION

The detection of low-levels of biological and inorganic materials in biological samples, in the body or in the environment is frequently difficult. Assays for this type of detection involve multiple steps which can include binding of a primary antibody, several wash steps, binding of a second antibody, additional wash steps, and depending on the detection system, additional enzymatic and washing steps. Such assays further suffer from lack of sensitivity and are subject to inaccuracies. For instance, traditional immunoassays have false negative results of up to 30% when detecting infections.

Molecular probe assays, although sensitive, require highly skilled personnel and knowledge of the nucleic acid sequence of the organism. Both the use of nucleic acid probes and assays based on the polymerase chain reaction (PCR) can only detect nucleic acid which require complicated extraction procedures and may or may not be the primary indicator of a disease state or contaminant. Both types of assay formats are limited in their repertoire in cases where little information is available for the entity to be detected.

Current noninvasive methods to measure a patient's physical parameters, such as CAT or MRI, are expensive and are often inaccessible. Thus, the monitoring of many medical problems still requires tests, which can be slow and expensive. The time between the actual test and the confirmation of the condition may be very important. For example, in the case of sepsis, many patients succumb before infection is confirmed and the infecting organism identified, thus treatment tends to be empirical and less effective. Another example is in screening the blood supply for pathogens.

Verification of a pathogen free blood supply requires a number of labor intensive assays. In the case of HIV-1, the virus that causes AIDS, the current assays screen for anti-HIV antibodies and not the virus itself. There is a window lasting up to many weeks after exposure to the virus in which antibodies are not detectable, and yet the blood contains large amounts of infectious virus particles. Clark et al., 1994, *J. Infect. Dis.* 170:194–197; Piatak et al., 1993, *Aids Suppl.* 2:S65–71. Thus, screening of the blood supply is not only time-consuming and slow, it may also be inaccurate.

Similarly, the ability to detect substances in the environment, such as airborne and waterborne contaminants is of great importance. For example, it would be desirable to monitor groundwater, to control industrial processes, food processing and handling in real-time using an inexpensive versatile assay. However, current methods are not suited for such "on-line" monitoring.

There are several reasons why current methods are limited. First, access to sufficient amounts of the material to be detected may be difficult. For example, the detection of biological materials can be difficult as the biological materials of interest are often sequestered inside a body, and large quantities can be difficult to obtain for ex vivo monitoring. Therefore, sensitive assays for use on small amounts of material are necessary. This indicates that a method of amplifying the signal is required. Amplification methods have been established for detection of nucleic acids but this is not the case for antigen detection methods.

A second problem is that sensing may be difficult in real-time because the target materials may be present in such small quantities that detection of their presence requires time-consuming, expensive and technically-involved processes. For example, in the case of bacterial infections in the blood, sepsis, there may be only 1–2 bacteria in a 1–10 ml blood sample. Current methods require that the bacteria are grown first in order to be detected. Askin, 1995, *J. Obstet. Gynecol. Neonatal. Nurs.* 24:635–643. This time-lag may be detrimental as delaying treatment or mistreating diseases may mean the difference between life and death.

Others have attempted to avoid these limitations by using radioactive or fluorescent tags in combination with antibodies (Harlow et al., (1988), *Antibodies. A Laboratory Manual* (Cold Spring Harbor, N.Y.: Cold Spring Harbor Laboratory Press). Antibody-based assays typically involve binding of a primary antibody to the target molecule, followed by a series of washing steps to remove all unbound antibodies. Specific binding is typically detected using an identifier molecule, such a labeled secondary antibody directed against the primary antibody. This step is also followed by multiple wash steps. Alternatively, the primary antibody may be directly attached to a detectable label. Suitable labels have included radioactive tracers, fluorescent tags, and chemiluminescent detection systems. Harlow, et al., 1988, *Antibodies. A Laboratory Manual* (Cold Spring Harbor, N.Y.: Cold Spring Harbor Laboratory Press).

The series of steps required using such antibody-based assays to generate a specific signal are time consuming and labor intensive. Furthermore, these type of assays are limited to the detection of antigens fixed to some type of matrix. Examples of this type of detection system include Western blots, immunohistochemistry, and ELISA. The highest sensitivity is currently achieved using radioisotopic and chemiluminescent tags. However, sensitivity, i.e., specific signal over background, of these detection systems frequently remains a limiting factor.

Similarly, background radiation places limits on the sensitivity of radioactive immunoassay techniques. In addition, these techniques are time-consuming and expensive. Finally, radioactive approaches are hostile to the environment, as they present significant waste disposal problems.

Another approach to monitoring substances involves the use of light. Light has the advantage that it is easily measurable, noninvasive and quantitative. Von Bally et al., (1982), *Optics in Biomedical Sciences: Proceedings of the International Conference* (Berlin, N.Y.: Springer-Verlag).

Traditional spectroscopy involves shining light into substances and calculating concentration based upon the absorbance or scattering of light. Von Bally et al., (1982), *Optics in Biomedical Sciences: Proceedings of the International Conference* (Berlin, N.Y.: Springer-Verlag). Optical techniques detect variations in the concentration of light-absorbing or light scattering materials. Von Bally et al., (1982), *Optics in Biomedical Sciences: Proceedings of the International Conference* (Berlin, N.Y.: Springer-Verlag). Near-infrared spectroscopy has proved to be a relatively safe form of radiation that functions well as a medical probe, since it can penetrate into tissues. Further, it is well-tolerated in large dosages. For example, light is now used to calculate the concentration of oxygen in the blood (Nellcor) or in the body (Benaron image), or even to monitor glucose in the body (Sandia). Benaron and Stevenson, 1993, *Science* 259:1463–1466; Benaron et al., 1993, in: *Medical Optical Tomography: Functional Imaging and Monitoring*, G. Muller, B. Chance, R. Alfano and e. al., eds. (Bellingham, Wash. USA: SPIE Press), pp. 3–9; Benaron and Stevenson, 1994, *Adv. Exp. Med. Biol.* 361:609–617. However, current techniques are limited in that many substances do not have unique spectroscopic signals which can be optically assessed easily and quantitatively. Von Bally et al., (1982), *Optics in Biomedical Sciences: Proceedings of the International Conference* (Berlin, N.Y.: Springer-Verlag). Furthermore, the detection of substances at low concentration is frequently hampered by high background signals, especially in biological media such as tissues. Von Bally et al., (1982), *Optics in Biomedical Sciences: Proceedings of the International Conference* (Berlin, N.Y.: Springer-Verlag).

Over the past years, assays based on light emission, for example chemiluminescence (Tatsu and Yoshikawa, 1990, *Anal. Chem.* 62:2103–2106), have attracted increasing attention due to the development of extremely sensitive methods for detecting and quantifying light. Hooper et al., 1994 *J. Biolumin. Chemilumin.* 9:113–122. One example of a biomedical research product using chemiluminescence is the ECL detection system (Amersham) for immunoassays and nucleic acid detection.

The use of biological sources of light, bioluminescence, for biological assays has paralleled development of chemiluminescent detection, as similar devices for light detection are required. Kricka, 1991, *Clin. Chem.* 37:1472–1481. One of the most commonly employed biological sources of light is luciferase, a light-generating enzyme synthesized by a range of organisms, including *Photinus pyralis* (American firefly), *Renilla reniformis* (phosphorescent coral), and Photobacterium (luminescent bacterial species). Generally, luciferase is a low molecular weight oxidoreductase, which catalyzes the dehydrogenation of luciferin in the presence of oxygen, ATP and magnesium ions. During this process, about 96% of the energy released appears as visible light. For review, see, Jassim et al., 1990, *J. Biolumin. Chemilumin.* 5:115–122.

The sensitivity of photon detection and the ability to engineer bacteria and other cells to express bioluminescent proteins permit the use of such cells as sensitive biosensors in environmental studies. Guzzo et al., 1992, *Toxicol. Lett.* 64:687–693; Heitzer et al., 1994, *Appl. Environ. Microbiol.* 60:1487–1494; Karube and Nakanishi, 1994, *Curr. Opin. Biotechnol.* 5:54–59; Phadke, 1992, *Biosystems* 27:203–206; Selifonova et al., 1993, *Appl. Environ. Microbiol.* 59:3083–3090. For example, Selifonova et al. describe biosensors for the detection of pollutants in the environment. More specifically, using fusions of the Hg(II) inducible Tn21 operon with the promoterless luxCDABE from *Vibrio fischeri*, highly sensitive biosensors for the detection of Hg(II) have been constructed.

In addition to systems where bioluminescence is used as a detection method of a specific condition, e.g., the presence of Hg(II), supra, constitutive expression of luciferase has been employed as a marker to track viability of bacterial cells, as the luciferase assay is dependent on cell viability. For example, constitutive expression of luciferase has recently been employed in a bacterial disease model for testing of drugs and vaccines. Specifically, using an enhanced luciferase-expressing *Mycobacterium tuberculosis* strain has been employed to evaluate antibacterial activity in mice. Hickey et al., 1996, *Antibacterial Agents and Chemotherapy* 40:400–407.

However, currently-available biosensors are limited to the detection of those molecules for which an endogenous bacterial receptor exists. In contrast, the present invention enables the generation of biosensors selective for any antigen or substance which can be selectively recognized by an antibody or receptor. Specifically, the present invention combines the selectivity of ligand-specific binding and the versatility of the antibody repertoire with the sensitivity of bioluminescent detection, employing entities that specifically respond with photon emission to predetermined ligands. The approach of the present invention thus permits the generation of extremely sensitive biodetectors for the development of a wide variety of assays detecting any number of commercially important molecules.

III. SUMMARY OF THE INVENTION

The present invention is directed to targeted ligand-specific biodetectors for detecting and monitoring selected substances. More specifically, the biodetectors of the present invention comprise (1) a signal converting element, (2) a transducer, (3) a responsive element, and (4) a reporter gene. The signal converting element comprises an extracellular ligand-specific moiety and an intracellular signal transforming domain. The extracellular ligand-specific moiety specifically recognizes a selected substance. Recognition of the substance by the extracellular ligand-specific moiety activates the intracellular signal transforming domain. The activated signal-transforming domain in turn activates the transducer, which in its activated form is capable of binding to and activating the responsive element. The responsive element, typically a promoter, is operatively linked to the reporter gene, which encodes a polypeptide with unique properties that are easily detected, e.g., optically. Thus, the biodetectors of the invention convert the action of binding to a target substance, i.e., a ligand, into a detectable signal.

In a general embodiment, the signal converting element is a fusion protein where the extracellular ligand-specific moiety and the intracellular signal transforming domain are heterologous to one another (i.e., are derived from different proteins). In a preferred embodiment, the extracellular ligand-specific moiety is an antibody fragment, such as a single chain variable fragment (ScFv).

In yet another embodiment, of the invention, the intracellular signal transforming element is derived from a membrane signal sensor molecule. The membrane signal sensor may be selected from the group consisting of the "sensor" of a bacterial two component regulatory system, a eukaryotic receptor, and a prokaryotic receptor. In a specific embodiment, the intracellular signal transforming domain comprises the 3' end of the phoQ gene, which encodes the active or signal transforming portion of PhoQ, the "sensor" of the PhoQ/PhoP bacterial two component regulatory system. In a more specific embodiment, the intracellular signal transforming domain comprises the cytoplasmic tail of PhoQ, defined as amino acids 219–487 of the PhoQ polypeptide sequence. In another specific embodiment, the intracellular signal transforming domain comprises the cytoplasmic tail of PhoQ along with the immediately adjacent transmembrane segment, together defined as amino acids 190–487 of the PhoQ polypeptide sequence (Miller, et al., 1989, *Proc Natl Acad Sci* 86:5054–5058).

In another embodiment, the signal converting element further comprises a membrane anchor positioned between the between the extracellular ligand-specific moiety and the intracellular signal transforming domain. In a specific embodiment, the membrane anchor is derived from *E. coli* cell envelope component PAL. In yet another embodiment, the signal converting element further comprises an N-terminal leader sequence positioned upstream of the extracellular ligand-specific moiety.

In another general embodiment, the responsive element comprises a transcription control element which is activated by the active form of the transducer. One embodiment of the invention thus includes promoters and/or transcription activators which control transcription in two-component systems. In a particular embodiment, the responsive element comprises the phoN promoter.

In still another general embodiment, the biodetector comprises an intact bacterial cell transfected as detailed herein. In one embodiment, the biodetector is a Gram-positive bacterial cell. Such a biodetector may be selected from the group consisting of Streptococcus, Staphylococcus, Listeria, Clostridium, Bacillus, Tuberculosis, and Corynebacteria. In another embodiment, the biodetector is a Gram-negative bacterial cell. Such a biodetector may be selected from the group consisting of Escherichia, Salmonella, Pseudomonas, Helicobacter, Shigella, Proteus, Bordetella, Neisseria, Haemophilus, Bacteriodes, Vibrio, Brucella, Campylobacter, Rickettsia, Enterococci, Klebsiella, Spirochetes, and Yersinia. Preferred embodiments of Gram negative biodetectors comprise Escherichia and Salmonella.

In still another embodiment of the invention, the substance that the biodetector is designed to detect is selected from the group consisting of bacteria, bacterial products, viruses, protein, sugar, lipid, liposaccharide and polysaccharide.

In another aspect, the invention includes a biodetector for the detection of a selected substance. The biodetector comprises (a) a signal converting element, comprising an extracellular ligand-specific moiety and an intracellular signal transforming domain, wherein the extracellular ligand-specific moiety specifically recognizes the selected substance, which recognition activates the intracellular signal transforming domain; (b) a transducer, wherein the transducer has an inactive and an active form which are distinct from each other, and wherein the activated intracellular signal transforming domain converts the inactive form of the transducer into the active form of the transducer; and (c) a responsive element, wherein the responsive element is bound and activated by the active form of the transducer, resulting in a detectable signal.

In one embodiment, the responsive element further comprises a nucleic acid encoding one or a plurality of gene product(s), which gene product or gene products produce the detectable signal, and wherein the nucleic acid is operatively linked to the transcription control element. In a more specific embodiment, the detectable signal is visible light. In another specific embodiment, the gene product is detectable by means selected from the group consisting of bioluminescence, colorimetric reactions and fluorescence. In a more specific embodiment, the gene product is detectable by means of bioluminescence. In yet a more specific embodiment, the nucleic acid comprises a luciferase operon.

Other specific embodiments of this aspect of the invention include those summarized above for other biodetectors made in accordance with the invention.

Also included in the invention is a library of biodetectors, where the biodetectors have characteristics, in different specific embodiments of such a library, as described above. In a general embodiment, the biodetectors in such a library comprise a plurality of bacterial cells transfected with a mixture of cDNA molecules encoding antibody variable region genes, Fab fragments, F(ab')$_2$ fragments, or single chain variable fragments (ScFvs). The library preferably includes at least about 1000 different biodetectors, more preferably at least about 10,000 different biodetectors, and even more preferably at least about 100,000 different biodetectors.

The present invention is further directed to methods of using such biodetectors for detecting and monitoring selected substances with a high sensitivity and specificity (selectivity). The methods using the biodetectors of the invention include the detection of contaminants in the food and agriculture industries, diagnosis and monitoring in medicine and research, detection of poisons or pathogenic contaminants in the environmental or defense setting, and drug testing. Accordingly, the invention includes a method for detection of a selected substance. The method comprises the steps of (a) generating a biodetector; (b) adding the biodetector to a sample; (c) measuring and quantifying the detectable signal; and correlating the levels of the detectable signal with the presence and quantity of the substance. The biodetector generated in step (a) comprises (i) a signal converting element, comprising an extracellular ligand-specific moiety and an intracellular signal transforming domain, wherein the extracellular ligand-specific moiety specifically recognizes the selected substance, which recognition activates the intracellular signal transforming domain; (ii) a transducer, wherein the transducer has an inactive and an active form which are distinct, and wherein the inactive form is converted into the active form by the activated intracellular signal transforming domain; and (iii) a responsive element, wherein the responsive element is bound and activated by the active form of the transducer, resulting in a detectable signal.

In one embodiment, the responsive element of the biodetector in the method comprises a transcription control element which is activated by the active form of the transducer. In another embodiment, the responsive element further comprises a nucleic acid encoding one or a plurality of gene products which gene product or gene products produce the detectable signal, and wherein the nucleic acid is operatively linked to the transcription control element. In a preferred embodiment, the detectable signal is light. The gene product in such an embodiment may be detected by a means selected from the group consisting of bioluminescence, calorimetric reactions and fluorescence. In a specific embodiment, the nucleic acid comprises a luciferase operon. In a more specific embodiment, the light detection system is selected from the group consisting of luminometer, spectrophotometer, fluorimeter, and a CCD detector.

In another embodiment, the biodetector or the sample in the method is fixed on a solid support. In yet another embodiment, the method further includes fixing a series of biodetectors in an ordered array on a solid support such that a variety of substances comprised in a sample can be detected.

In another aspect, the invention includes an expression vector useful for making a biodetector. The vector comprises (i) a cloning site for insertion of a DNA fragment encoding an extracellular ligand-specific moiety, and (ii) a first DNA fragment encoding an intracellular signal transforming domain. Preferably, the vector is capable of expressing a fusion protein comprising (a) a polypeptide encoded by a DNA sequence inserted at said cloning site, and (b) the intracellular signal transforming domain. In one embodiment, the vector further comprises, between the cloning site and the first DNA fragment, a second DNA fragment encoding a membrane anchor. In another embodiment, the vector further comprises, upstream of the cloning site, a third DNA fragment encoding an N-terminal leader sequence. In another embodiment, the vector further comprises, inserted at the cloning site, a fourth DNA fragment encoding an extracellular ligand-specific moiety. In another embodiment, the extracellular ligand-specific moiety comprises an antibody fragment. In another embodiment, the first DNA fragment encodes a polypeptide comprising the cytoplasmic tail of PhoQ.

IV. BRIEF DESCRIPTION OF THE FIGURES

Figure 4:
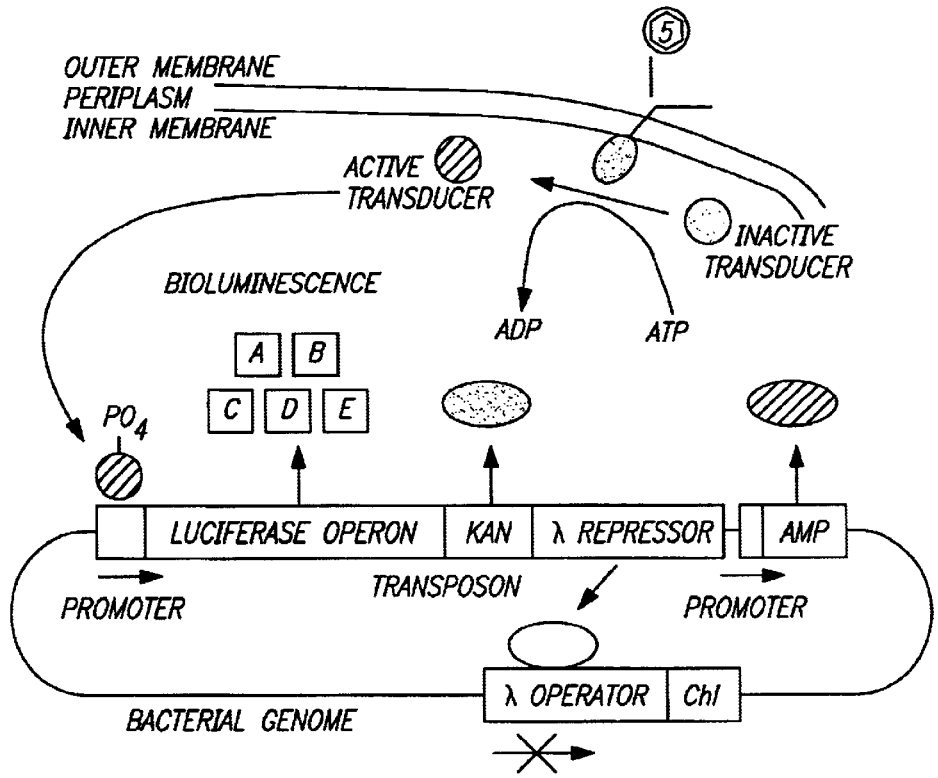
Figure 4:
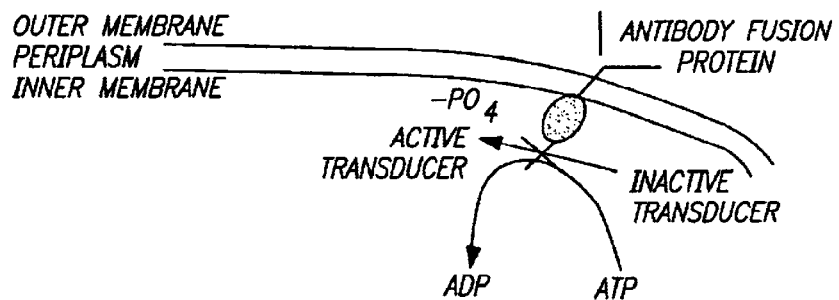

FIG. 4 depicts a biodetector generated by the integration of a transposon in the bacterial genome as specified in EXAMPLE 1. The bacterial luciferase operon encodes five proteins (from genes A, B, C, D and E) that together can produce bioluminescence. Chl, chloramphenicol resistance gene; Kan, kanamycin resistance gene; Amp, Ampicillin resistance gene; $PO_4$, phosphate group (as activator of the transducer).

Figure 5:
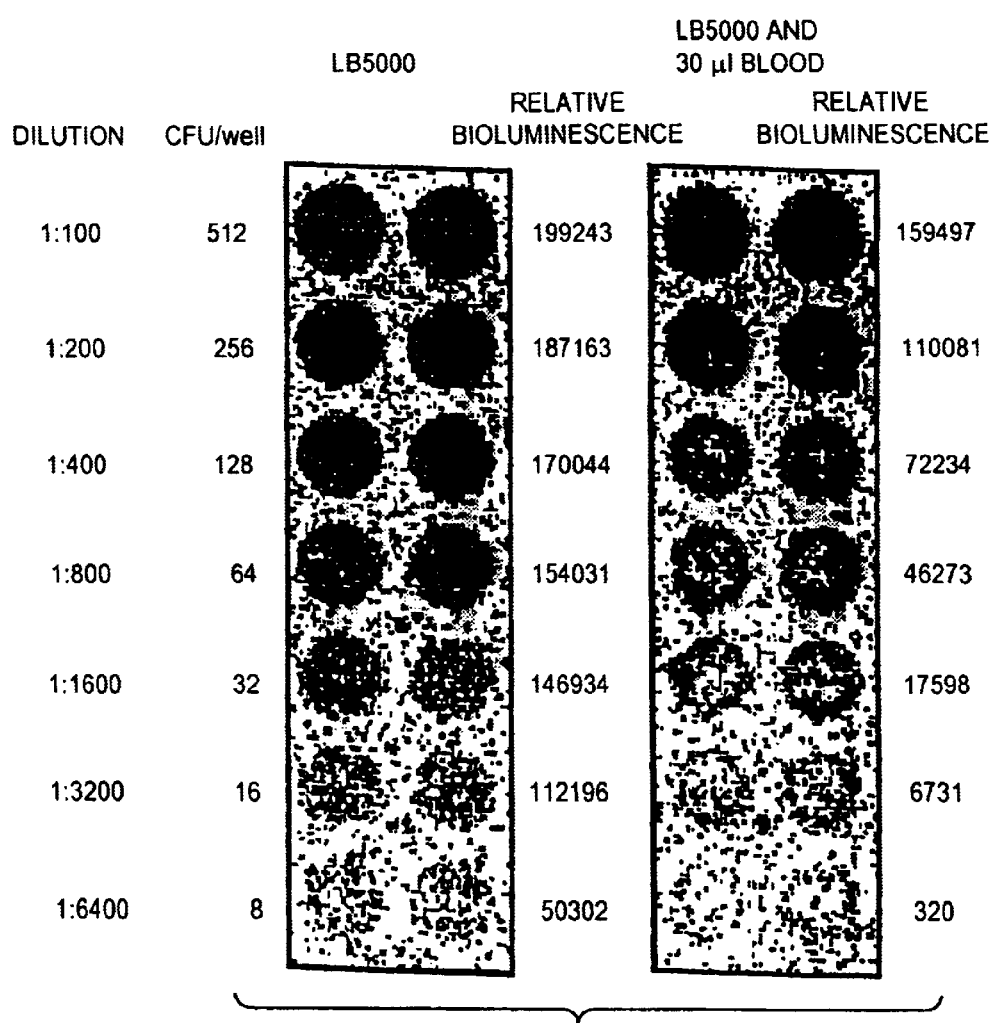

FIG. 5 depicts the effect of human blood on the light emission from bioluminescent Salmonella, demonstrating near single cell detection.

Figure 6:
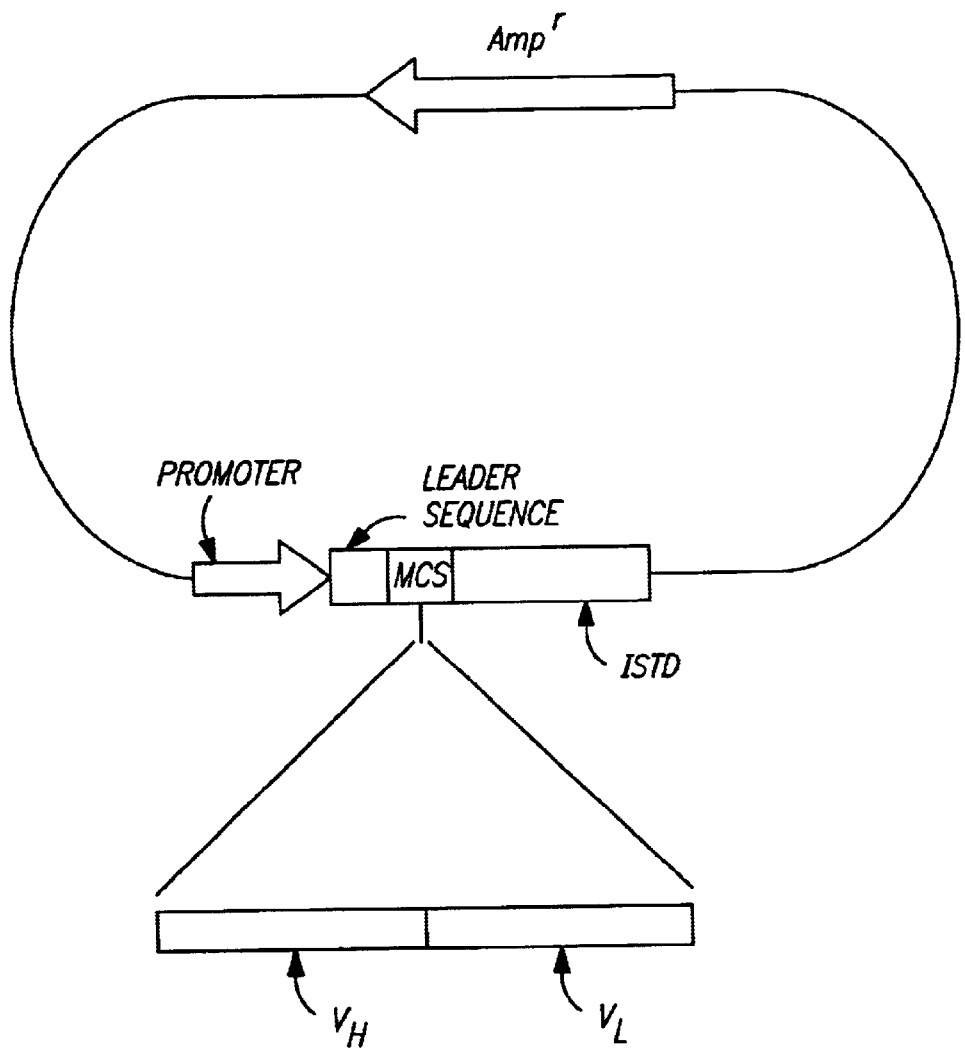

FIG. 6 depicts an expression vector according to the invention. The vector contains an antibiotic (Ampicillin) resistance gene ($Amp^r$), a promoter, a DNA sequence encoding an N-terminal leader sequence, a multiple cloning site for insertion of a DNA encoding an antibody fragment, such as a fragment comprising a variable heavy chain ($V_H$) and a variable light chain ($V_L$) region, and a DNA fragment encoding an intracellular signal transforming domain (ISTD).

V. Definitions

Unless otherwise indicated, all terms used herein have the same meaning as they would be understood by one skilled in the art.

The term "target molecule" as used herein describes a substance that is to be detected and/or quantified.

The term "luciferases" as used herein, unless otherwise stated, includes prokaryotic and eukaryotic luciferases as well as variants with varied or altered physical and/or emission properties.

The term "biodetector" as used herein refers to an entity that responds with an optical signal to the binding or otherwise interacting with the target molecule.

The term "optical signal" as used herein refers to any biochemical reaction or substance that can be distinguished using light monitoring techniques. This includes photon emission, fluorescence, and absorbance.

The term "light" as used herein, unless otherwise stated, refers to electromagnetic radiation having a wavelength between about 220 nm and about 1100 nm.

The term "promoter induction" as used herein refers to an event that results in direct or indirect activation of a selected inducible genetic element.

VI. DETAILED DESCRIPTION OF THE INVENTION

A. General Overview of the Invention

The present invention is directed to targeted ligand-specific biodetectors for detecting and monitoring selected substances, including microorganisms and their products/by-products, chemical compounds, molecules, and ions, for a wide range of applications. In a preferred embodiment, the biodetectors of the present invention combine the specificity and selectivity of ligand-specific binding with the sensitivity of bioluminescent detection by employing entities that specifically respond to the binding of a predetermined ligand with photon emission. Thus, the approach of the present invention permits the generation of sensitive biodetectors for the development of a wide variety of assays detecting and monitoring any selected substance.

More specifically, the biodetectors of the present invention provide for the coupling of ligand-specific binding, via a "molecular switch," i.e., a signal transduction, with the activation of a detectable reporter molecule in response to ligand binding. The biodetectors of the present invention may consist of viable biological entities, such as bacteria, or abiotic entities, such as liposomes. As a general scheme, the biodetectors are characterized by their ability to specifically recognize a ligand and convert binding to the ligand to a measurable signal, such as light emission. For example, bacteria may be employed as ligand-specific biodetectors, which specifically respond with photon emission to predetermined ligands.

The biodetectors of the present invention permit highly sensitive detection of a wide variety of substances, for example microbes in human blood (e.g., viruses and bacteria), toxic molecules, ions, cancer cells, antigens, small molecules (e.g., glucose), oxygen, and metals. Further, the present invention provides for the use of such biodetectors in a wide variety of assays to detect any selected substance.

Generally, the biodetectors of the present invention comprise a signal converting element, comprising an extracellular ligand-specific binding moiety, which is coupled to an intracellular signal transforming domain which is capable of activating a transducer component. The transducer component in its active form is capable of activating a responsive element, such as a promoter which is operatively linked to a reporter gene (e.g., a luciferase gene), encoding for a diagnostic polypeptide with unique properties that are readily detectable. Thus, the biodetectors of the invention convert the binding of a target substance, i.e., a ligand, into a detectable signal. In preferred embodiments of the invention, the signal generated by the biodetector is light and is detected by a light-detecting device. Accordingly, based upon this interaction, the targeted ligand(s) may be quantified and identified.

B. Biodetectors

The biodetectors of the invention are characterized in that they generate a detectable signal in response to either the presence of a targeted substance in vivo or in vitro.

In one specific embodiment, light is the detectable signal generated by the biodetector in response to the presence of the targeted substance. As there is virtually no background light coming from normal tissues and other organic or inorganic materials, the sensitivity of the system is limited only by the background noise of the biodetector. More specifically, the ligand-specific biodetectors of the present invention include a ligand-specific domain, which, via a "molecular switch," is linked to a reporter gene encoding a detectable protein. The reporter gene is thus activated in response to binding of the ligand to the ligand-specific domain. The ligand-specific binding moiety may be any antibody which selectively binds to the substance of interest. The "molecular switch" is a signal transducing component which couples ligand binding to the activation of a responsive element. The transducing molecule can be derived from any two component regulatory system of bacteria, including the phosphate regulon, or any eukaryotic transducer. The responsive element may be an inducible promoter, operatively linked to a reporter gene. Transcription and translation of this reporter gene will result in a gene product, e.g., luciferase, which produces a detectable signal, e.g., light. The signal is detected by suitable means; in the case the signal is light, this means will be a photodetection device.

For example, imaging of the light-emitting biodetector entities may involve the use of a photodetector capable of detecting extremely low levels of light—typically single photon events. If necessary, localization of signal could be determined by integrating photon emission until an image can be constructed. Examples of such sensitive photodetectors include devices (such as microchannel plate intensifiers and photomultiplier tubes) that intensify the single photon events. Intensifiers may be placed before a camera. In addition, sensitive cameras (cooled, e.g., with liquid nitrogen) that are capable of detecting single photons over the background noise inherent) in a detection system may also be used.

Once a photon emission image is generated, it is typically superimposed on a "normal" reflected light image of the subject to provide a frame of reference for the source of the emitted photons. Such a "composite" image is then analyzed to determine the location and/or amount of a target in the subject. In most circumstances images of the light source are not required. Simple quantitation of the numbers of photons emitted from a sample (as detected for example by a luminometer) indicate the concentration of the light emitting reporter. The number of photons would therefore be proportional to the amount of targeted-ligand that a specific detector is sensing. Without the constraints imposed by the need for an image, detectors can be placed in very close proximity to the light-emitting biodetector thus optimizing the optical detection and sensitivity of the assay. Microchannel plate intensifiers can be used in such a configuration resulting in single photon detection. Such a device is currently manufactured by Hamamatsu Corporation. In the Hamamatsu system ATP concentrations from single cells can be assayed by spraying lysis buffer, luciferase and the substrate, luciferin, on immobilized cells.

Figure 1:
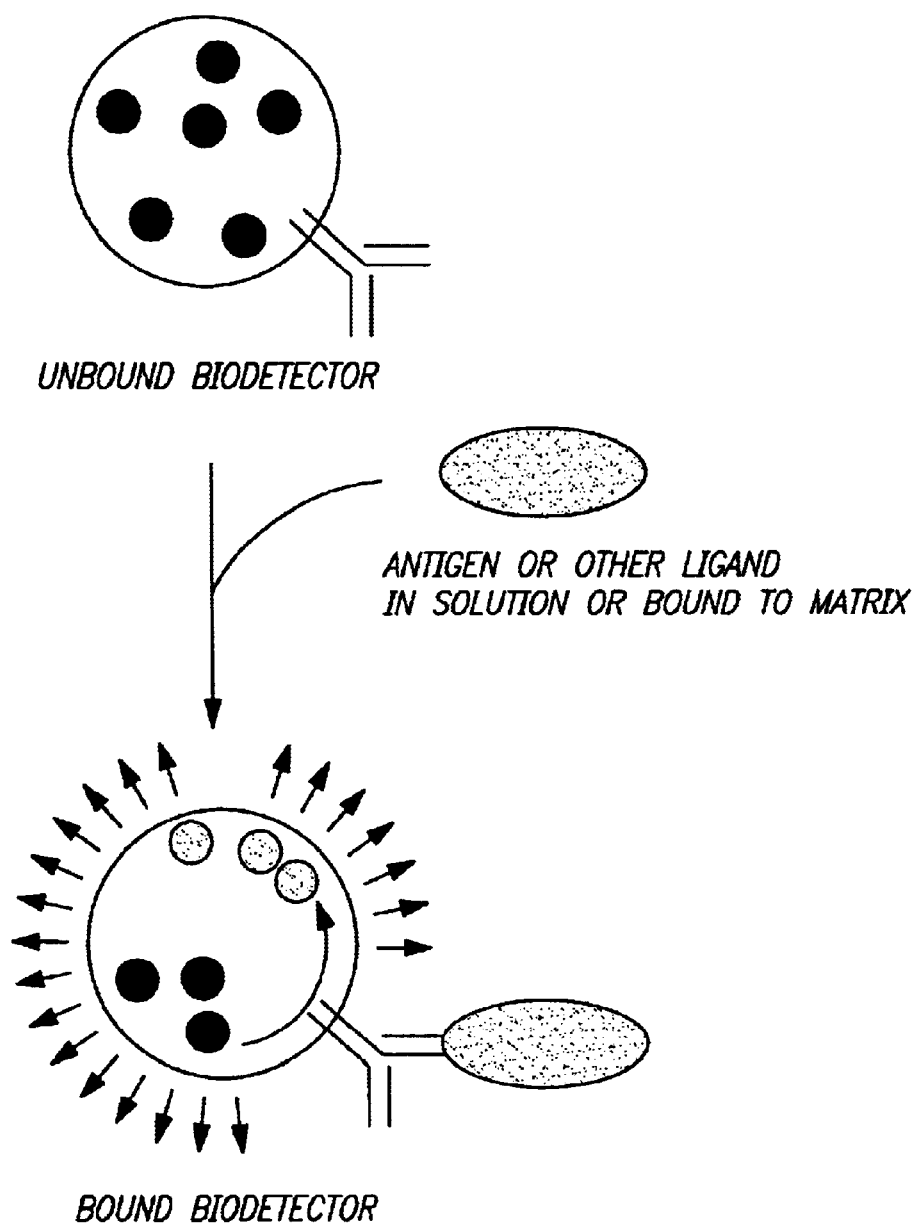
FIG. 1 depicts a generic model demonstrating the main components of a biodetector. A biodetector consisting of an entity possessing sensing ("Y-shaped" structure on surface), transducing components (part of "Y-shaped" structure inside of biodetector) and light-emitting components (small circles).
Figure 2:
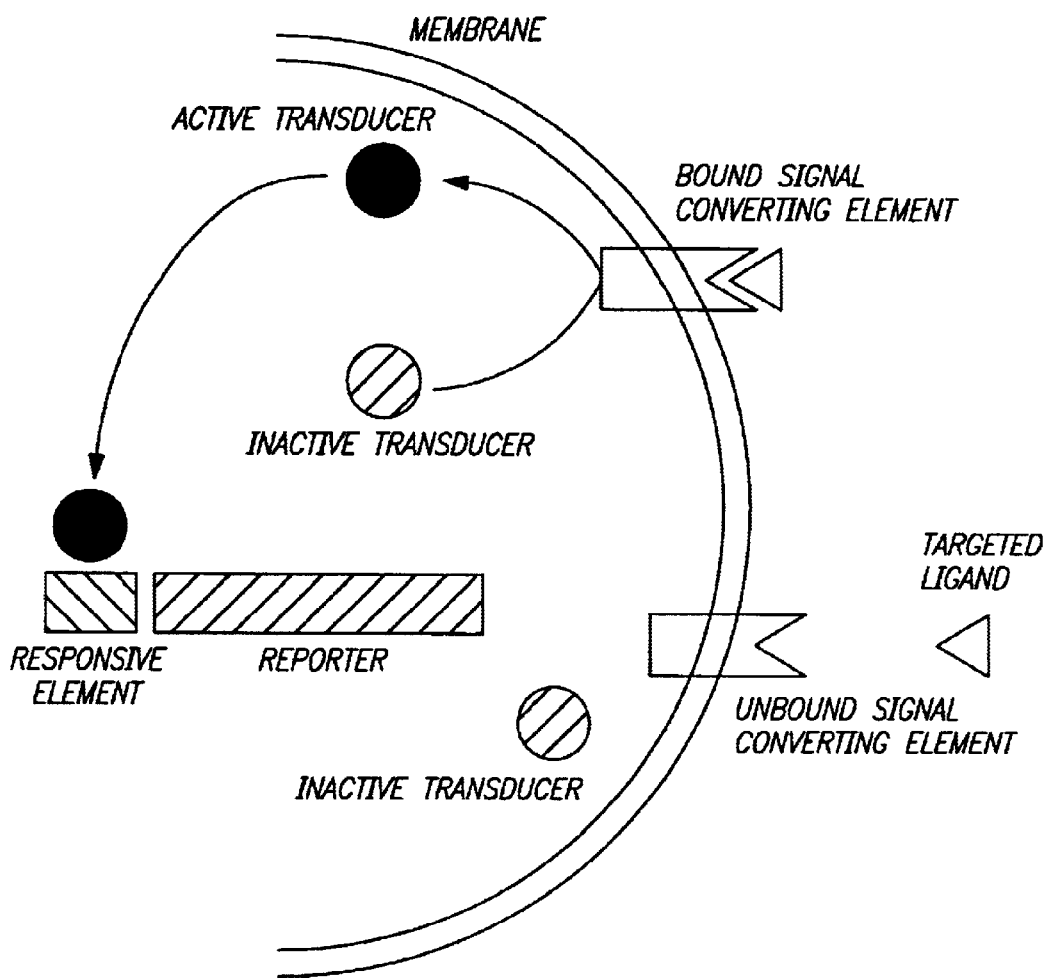
FIG. 2 depicts a more specific scheme of a biodetector on the molecular level.

The generic mechanism of a ligand-specific biodetector is shown in FIG. 1. The biodetector is combined with a gas, solution or support matrix that is to be tested for the presence of a selected substance or ligand. If such gas, solution or support matrix contains the selected antigen or ligand, the biodetector binds to it and generates a detectable signal, shown in FIG. 1 as light represented by outward arrows. FIG. 2 shows the molecular mechanism of a preferred biodetector more specifically. In the depicted example, the biodetector is a bacterial cell expressing a transmembrane target specific signal converting element, comprising an extracellular ligand-specific binding moiety, e.g., an antibody, which is coupled to an intracellular signal transforming domain. The target specific signal converting element is integrated in a membrane, e.g., a bacterial membrane, which separates an "extracellular" compartment from an "intracellular" compartment. The ligand-specific moiety (e.g., an ScFv) is capable of binding to a selected substance, which triggers the activation of the intracellular signal transforming domain (e.g., a signaling portion of PhoQ). The activated intracellular signal transforming domain in turn converts an inactive transducer into an active transducer. The transducer is characterized by its capability to bind, when converted to its active form, to a promoter element, which is operatively linked to a reporter gene. Transcription and translation of the reporter gene or operon results in a gene product which produces a detectable signal, such as light. In preferred embodiments of the invention, the reporter is a luciferase gene or operon, which produces visible light and can easily be monitored, measured and quantified with high sensitivity. Alternatively, the signal transforming domain could act directly on a modified reporter molecule. The reporter molecule would be modified to be expressed in an inactive state which can then be activated through its interaction with the signal transforming domain directly.

The biodetectors, providing a "light switch" that responds to a predetermined selected substance presents a number of advantages over current methodologies. First, the switch allows for detection of antigens, present in complex mixtures and eliminates the need to wash off unbound antibodies, thus simplifying the detection. Since ligand bound to antibody turns on light and since there is no background light in the sample, no washing is necessary to reduce signal to noise ratio, reduced noise increases sensitivity, and only specific interaction turns on the light. Once bound to a ligand, an enzymatic cascade is activated that serves to transmit the signal.

Moreover, if the targeted ligand is abundantly expressed on the surface of, for example, pathogenic microbes, many biodetecting bacteria will bind to a single target, thus serving to amplify the signal and result in extremely sensitive detection systems.

Furthermore, as the ligand-specific domain of the signal converting element of the biodetector system may be exchanged like a cassette, an unlimited number of biodetectors can be generated to recognize any desired or selected substance. Thus, the biodetectors of the present invention provide a flexible, generic system that can be adapted to recognize any selected substance, out of a wide variety of choices. Biodetectors targeting a substance of interest can rapidly be developed.

Figure 3:
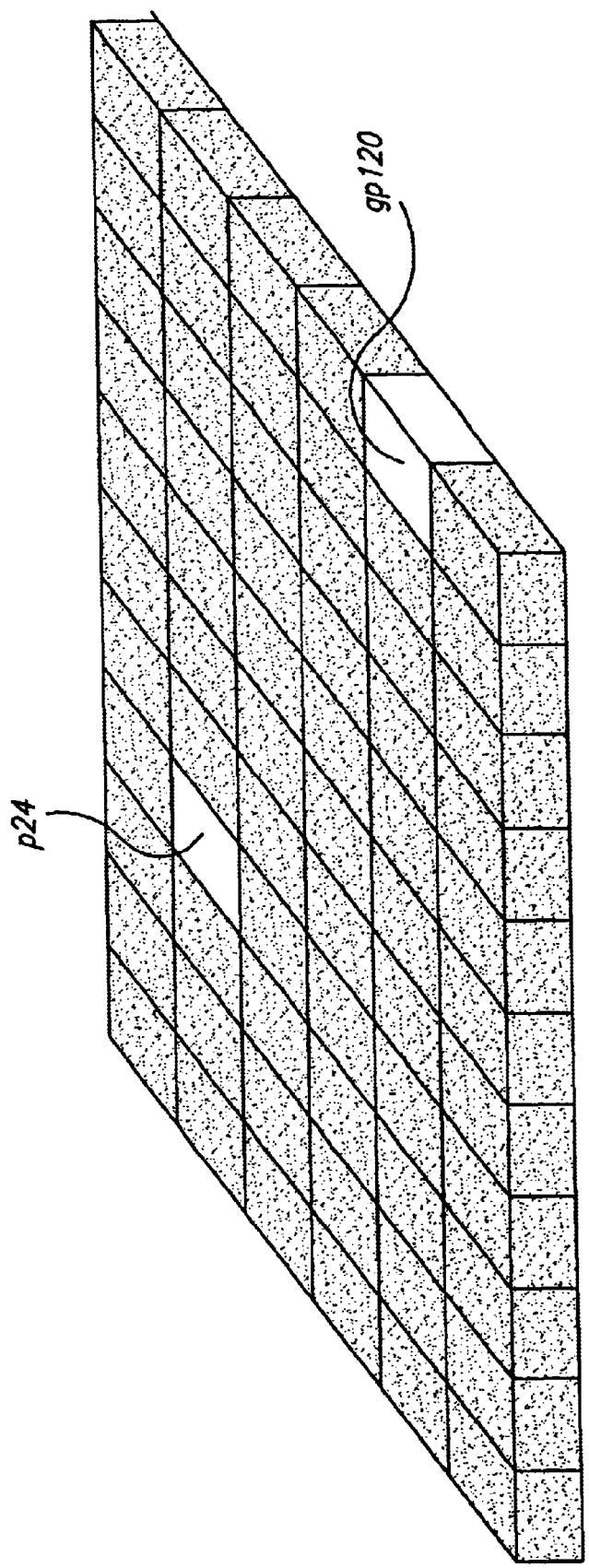
FIG. 3 depicts an ordered array of biodetectors on a solid support such that a variety of substances in a single sample can be detected simultaneously.

The biodetectors of the invention are versatile as they are effective in vivo, in solution, or on fixed sensor plates. Furthermore, arrays of these biodetectors may be constructed, operating at different wavelengths or on different positions of a "biosensor chip," allowing for simultaneous monitoring and screening of multiple agents, genes, gene products, or other targets. See, FIG. 3. For example, the biodetectors may be assembled in a unique multi-detector array configuration for the purpose of constructing a system capable of a plurality of parallel analyses in a single step. For example, the biodetector may be placed on a gel that lies on top of a normal signal detecting instrument, which, in the case the generated signal is light, may be, e.g., a charge coupled device (CCD) chip. Due to the spatial recognition of signals by the CCD array, the biodetector array may provide for a light-based analysis using multiple different sensors placed in an array on one sensor chip. Thus, an analysis may be simultaneously performed for, e.g., blood type, HIV exposure, Hepatitis status, Lymphokine profiles and CMV positivity. Multiple types of infection can be rapidly and simultaneously screened.

If light is the signal produced by the reporter, the signal may be detected noninvasively, as light can be detected through, for example, tissue. See, U.S. Pat. No. 5,650,135, hereby incorporated by reference in its entirety.

Furthermore, as the biodetectors of the invention are biocompatible, and as such environmentally friendly, they have comparatively low developmental costs and a lower burden to the user, especially when compared with methods that may involve toxic waste, such as radioactivity-based assays.

A further significant advantage of the biodetectors of the invention is the reduction in time and labor needed to perform many diagnostics tests. A common, rate-limiting step in many testing and diagnostic fields is the need for an accurate sensing and detection system suitable for providing immediate information. Examples include screening of the blood supply for the AIDS virus and other blood borne pathogens, the study and evaluation of novel drugs in tissue culture or animal models, and the monitoring of therapeutic protein output after genetic therapy. For example, the mandatory screening of the blood supply for HIV and other agents currently requires numerous tests. An inexpensive, rapid, and specific sensor detecting numerous blood borne pathogens with built-in confirmatory tests could significantly streamline the process, thus reducing net cost to the user. Similarly, the evaluation of potential new drugs, known as lead compounds, by pharmaceutical companies now requires elaborate, expensive tissue culture and animal trials. An inexpensive sensor and related hardware to allow in vitro and in vivo monitoring of drug kinetics and effectiveness will have great value to drug companies searching for ways to streamline such lead compound development.

1. Entities Sheltering Biodetectors

The biological components of the biodetector may be contained in or otherwise may be attached to living or nonliving entities that stabilize the essential interactions. Configuration of these components as such results in a micro sensing system capable of detecting small quantities of ligands with great specificity and sensitivity.

Living Entitles. Most typically, the biodetector entity is a living cell which is genetically engineered to comprise all required components. Living entities include, but are not limited to, prokaryotes; eukaryotes; viruses; phage; transformed eukaryotic cells, such as transformed lymphocytes and macrophages; and established cell lines. Most typically, the entity is a genetically engineered bacterial cell, such as E. coli. Genetically-modified bacteria can be grown rapidly at low cost, thus the advantage of the use of living cells as biodetector entity is that pools of these biodetectors can be replicated and grown once the original biodetector is constructed.

The use of "living" biodetector entities has several advantages. First, it allows the growth of biodetectors at low cost, once the sensors are engineered. Second, a living biodetector can amplify the detected signal. For example, the binding of one antigen to the surface of the bacteria can trigger a series of light-generating substances to be made, each of which can produce light in a repetitive manner. Thus, the binding of one antigen that properly stimulates the system can result in the production of large amounts of photons from one living biodetector. Third, the small size of cell-based biodetectors allows for the binding of a limited quantity of a ligand or target to a plurality of such biodetectors, further amplifying the total detectable signal and increasing sensitivity.

Non-Living Entities. However, abiotic biodetectors may be generated as well. The biodetector system may be placed in an inanimate gel, in abiotic capsules and liposomes and as such be injected into the body, or mounted on plates. Further, any other entity capable of preserving vectoral metabolism such as a lipid bilayer may be employed.

2. The Signal-Converting Element

The signal converting element is composed of an "extracellular" portion selectively binding a specific substance and an "intracellular" portion capable of activating the transducer. Typically, the signal converting element will be a transmembrane fusion protein composed of an extracellular ligand-binding portion, e.g. an antibody, and an intracellular enzymatic portion, which is activated upon binding of the extracellular portion to a selected target. Accordingly, the signal converting element is designed to convert the action of recognizing and binding of a specific substance, i.e., ligand, into an intracellular signal, resulting in the activation of the transducer component, which, in turn, activates a promoter that drives the expression of the reporter protein.

The Ligand-Binding Domain. Substances which may be identified by the present invention include, but are not limited to, proteins, peptides, sugars, fatty acids, ions, microorganisms, including bacteria, viruses, parasites and fungi. Accordingly, the ligand-binding domain may be an antibody, an antibody fragment, cellular receptor or any other ligand-binding protein, such as Staphylococcus Proteins A and G, a macrophage Fc receptor, a carbohydrate moiety, or an ion-binding moiety, such as domains from sodium or potassium channels.

In specific embodiments, the ligand-binding domain is an antibody or a derivative thereof, including but not limited to polyclonal antibodies, monoclonal antibodies (mAbs), humanized or chimeric antibodies, single chain antibodies or fragments (ScFvs), Fab fragments, $F(ab')_2$ fragments, fragments produced by a Fab expression library, anti-idiotypic (anti-Id) antibodies, and epitope-binding fragments of any of the above. In particular the monoclonal antibody technology, phage display technology, and the more recent development of techniques for expressing functional antibodies in bacterial cells have increased the versatility and ease of identifying suitable ligand-binding domains for any desired target. The reference of Orum, et al., 1993, *Nucleic Acids Research* 21(19):4491–4498 teaches in detail the construction and use of ScFvs; the reference of Collet et al., 1992, *Proc. Nat'l. Acad. Sci.* U.S.A. 89:10026–10030 teaches a binary plasmid system for constructing antibody libraries. For additional details about the expression of antibodies in bacterial cells, see, among other places, Huse et al., 1989, *Science* 246:1275–1281.

Moreover, the source of the antibody coding regions is not limited to those cloned from hybridoma cell lines where the specificity of the antibody is known and is monoclonal in nature. Rather, large antibody libraries may be employed to generate the fusion proteins such that a large number of biodetectors for the detection of an indefinite range of antigens can be generated.

The Signal Transforming Domain. The signal transforming domain may consist of an enzyme or active domain of an enzyme that has any number of protein modifying functions which may include phosphorylation, dephosphorylation, methylation, acetylation and protease activity. Such enzymes include protein kinases, phosphorylases, phosphatases, protein methylases, acetylases, and proteases, among others. Particularly suitable signal transforming domains are derived from signal transduction pathways in bacteria (Parkinson, 1993, Cell 73:857), especially two-component systems. Two component systems consist of a transmembrane "sensor", typically located in the inner cytoplasmic membrane, which monitors some environmental parameter, and a cytoplasmic response regulator that mediates an adaptive response, usually via an alteration in gene expression. Such systems are referred to herein as "sensor/transducer" pairs, where the cytoplasmic regulator is the "transducer". Activation of the transducer is typically through phosphorylation by its cognate sensor. *E. coli* is thought to have about 50 such sensor/transducer pairs (Stock, et al., 1990, *Nature* 344:395–400). They include the Omp proteins involved in osmoregulation, proteins associated with nitrogen assimilation and proteins involved in chemotaxis.

The application of a two-component system to the present invention is illustrated with the PhoQ/PhoP system (Miller, et al., 1989, *Proc Natl Acad Sci* 86:5054–5058; Soncini, et al, 1995, *J Bacteriol* 177:4364–4371). The active domain of the bacterial phosphorylase, PhoQ, is linked in a gene fusion to a region of cDNA encoding antibody domains. As such, interaction of the expressed fusion protein with the targeted antigen (ligand) results in a conformational change in the antibody-phosphorylase fusion. This conformational change activates the specific phosphorylase activity which activates PhoP, a transducer protein, through a phosphorylation/dephosphorylation event. Active PhoP binds to and thus activates the PhoN promoter which is used to drive expression of the reporter operon lux. Of course, one skilled in the art may practice the invention by similarly adapting and utilizing the proteins from any suitable two-component system.

Vectors for Expressing the Signal Converting Element. The present invention also includes expression vectors useful for making biodetector such as those described herein. A vector according to this aspect of the invention typically comprises (i) a first DNA fragment encoding an N-terminal leader sequence, (ii) a multiple cloning site (MCS) for insertion of a DNA fragment encoding an extracellular ligand-specific moiety, and (iii) a second DNA fragment encoding an intracellular signal transforming domain. The N-terminal leader sequence can be any bacterial sequence that is effective to direct an expressed polypeptide at least part-way through the outer membrane of a bacterial cell. Such sequences are known in the art, e.g., the N-terminal leader sequence from the exported bacterial protein pectate lyase. The multiple cloning site contains at least two adjacent restriction endonuclease sites suitable for the insertion of a selected sequence, e.g., an EcoR I site and a Hind III site.

In one embodiment, the vector further comprises, between the cloning site and the second DNA fragment, a third DNA fragment encoding a membrane anchor, such as a DNA fragment encoding a modified form of *E. coli* cell envelope component PAL (Fuchs, et al., U.S. Pat. No. 5,591,604, issued Jan. 7, 1997). The vector also typically contains a selectable antibiotic resistance gene (e.g., Amp), and a promoter (e.g., a T3 or T7 promoter) operably linked upstream of the DNA encoding the N-terminal leader sequence. An exemplary vector according to this aspect of the invention is shown in FIG. 6.

The vector is useful for the construction of biodetectors, as detailed herein. DNA fragments encoding antibody fragments can be cloned into the MCS and expressed as fusion proteins having an N-terminal leader sequence adjacent the antibody fragment(s) adjacent a polypeptide functioning as the intracellular signal transforming domain.

3. Transducers

The transducer is activated by the signal converting element upon ligand binding. The transducer may be activated by phosphorylation, glycosylation, methylation electron transport, hydrogen transport, carboxylation, dehydrogenation, oxidation/reduction or any other chemical modification. The transducer may be any molecule that can recognize and respond to a change in conformation, electrical charge, addition or subtraction of any chemical subgroup, such as phosphorylation, glycosylation, and in turn is capable of triggering a detectable response. In embodiments wherein the the intracellular signal transforming element is derived from an endogenous signalling pathway, such as a bacterial two-component pathway, the transducer of the invention is typically the same transducer as is used in the endogenous pathway. Thus, in embodiments which employ an intracellular signal transforming domain derived from a C-terminal portion of PhoQ, the transducer is preferably PhoP that is endogenous to the bacterial cell sheltering the biodetector.

In specific embodiments of the invention, activation of the transducer triggers, directly or indirectly, the activation of a transcription control element, e.g., a promoter, to allow expression of a reporter gene or reporter operon. Transcription and translation of the reporter gene or operon in turn results in a gene product or gene products which produces a detectable signal, such as light. However, in alternative embodiments, activation of the transducer may directly result in a visible and measurable signal.

4. Responsive Elements

A responsive element according to the present invention is typically a transcription control element or promoter operatively linked to the reporter gene or operon. In a preferred embodiment, the activated transducer binds to the transcription control element or promoter and activates or turns on the promoter to initiate transcription of the downstream gene or operon. Regulatable promoters are well known in the art. One embodiment of the invention thus includes promoters and/or transcriptional activators which control transcription in two-component systems. In one specific embodiment, the responsive element comprises the phoN promoter, isolated, e.g., as described in Example 2A.

5. Reporter Genes And Operons

A wide range of reporter genes or reporter operons may be employed, including such which result in bioluminescence, calorimetric reactions or fluorescence. For example, reporter genes may encode for pigments (Bonhoeffer, 1995, *Arzneimittelforschung* 45:351–356) such as bacterial rhodopsin (Ng et al., 1995, *Biochemistry* 34:879–890), melanin (Vitkin et al., 1994, *Photochemistry and Photobiology* 59:455–462), aquorins (Molecular Probes, Seattle), green fluorescent protein (GFP, Clonetech, Palo Alto; Chalfie et al., 1994, *Science* 263:802–805; Cubitt et al., 1995, *TIBS* 20:448–455), yellow fluorescent protein (Daubner et al., 1987, *Proc. Natl. Acad. Sci. U.S.A.* 84:8912–8916), flavins, bioflavinoids, hemoglobin (Chance et al., 1995, *Analytical Biochemistry* 227:351–362; Shen et al., 1993, *Proc. Natl. Acad. Sci. U.S.A.* 90:8108–8112), heme (Pieulle et al., 1996, *Biochem. Biophys. Acta* 1273: 51–61), indigo dye (Murdock et al., 1993, *Biotechnology* 11:381–386), peridinin-chlorophyll-a protein (PCP) (Ogata et al., 1994, *FEBS Letters,* 356:367–371), or pyocyanine (al-Shibib and Kandela, 1993, *Acta Microbiologica Polonica* 42:275–280). Alternatively, reporter genes may encode for enzymes that can cleave a color absorbing substrate such as β-lactamase, luminescent and fluorescent proteins, enzymes with fluorescent substrates, or any other gene that encodes an optically active chemical or that can convert substrate to an optically active compound. In a further alternative, reporter genes may encode photoproteins. In each case, the reporter is operatively linked to an inducible promoter which is activated by the active form of the transducer component.

In a specific embodiment of the invention, bioluminescent reporters are employed.

Bioluminescence-Based Reporter Genes and Operons. Several types of bioluminescent reporter genes are known, including the luciferase family (e.g., Wood et al., 1989, Science 244:700–702). Members of the luciferase family have been identified in a variety of prokaryotic and eukaryotic organisms. Luciferase and other enzymes involved in the prokaryotic luminescent (lux) systems, as well as the corresponding lux genes, have been isolated from marine bacteria in the Vibrio and Photobacterium genera and from terrestrial bacteria in the Xenorhabdus genus, also called photorhalodus.

An exemplary eukaryotic organism containing a luciferase system (luc) is the North American firefly *Photinus pyralis*. Firefly luciferase has been extensively studied, and is widely used in ATP assays. cDNAs encoding luciferases from *Pyrophorus plagiophthalamus*, another species, click beetle, have been cloned and expressed (Wood et al., 1989, Science 244:700–702). This beetle is unusual in that different members of the species emit bioluminescence of different colors. Four classes of clones, having 95–99% homology with each other, were isolated. They emit light at 546 nm (green), 560 nm (yellow-green), 578 nm (yellow) and 593 nm (orange).

Luciferases require a source of energy, such as ATP and NAD(P)H, and a substrate, such as luciferin, decanal (bacterial enzymes) or coelentrizine and oxygen. The substrate luciferin must be supplied to the luciferase enzyme in order for it to luminesce. The substrate (e.g., luciferin or coelentrizine) may be applied externally or supplied by providing the enzymes for its synthesis. For external application of luciferin, the substrate may be dissolved n DMSO at a concentration of, e.g., 20 mM–200 mM. A convenient method for providing luciferin is to express the biosynthetic enzymes for the synthesis of the substrate decanal. In bacteria expressing these proteins, oxygen is the only extrinsic requirement for bioluminescence. In particular, the lux operon obtained from the soil bacterium *Xenorhabdus luminescence* (Frackman et al., 1990, *J. Bact.* 172:5767–5773) may be used as reporter operon, as it confers on transformed *E. coli* the ability to emit photons through the expression of the two subunits of the heterodimeric luciferase and three accessory proteins (Frackman et al., supra).

Optimal bioluminescence for *E. coli* expressing the lux genes of *X. luminescence* is observed at 37° C. (Szittner and Meighen 1990, *J. Biol. Chem.* 265:16581–16587; Xi et al., 1991, *J. Bact.* 173:1399–1405), which contrasts with the low temperature optima of luciferases from eukaryotic and other prokaryotic luminescent organisms (Campbell, 1988, *Chemiluminescence. Principles and Applications in Biology and Medicine* (Chichester, England: Ellis Horwood Ltd. and VCH Verlagsgesellschaft mbH)). Thus, the reporter operon may be chosen according to the nature and the requirements of a specific application. For example, the luciferase from *X. luminescence*, therefore, is well-suited for use as a marker for studies in animals.

Luciferase vector constructs can be adapted for use in transforming a variety of host cells, including most bacteria, and many eukaryotic cells. In addition, certain viruses, such as herpes virus and vaccinia virus, can be genetically-engineered to express luciferase. For example, Kovacs and Mettenlieter, 1991, *J. Gen. Virol.* 72:2999–3008, teach the stable expression of the gene encoding firefly luciferase in a herpes virus. Brasier and Ron, 1992, *Meth. in Enzymol.* 216:386–396, teach the use of luciferase gene constructs in mammalian cells. Luciferase expression from mammalian cells in culture has been studied using CCD imaging both macroscopically (Israel and Honigman, 1991, *Gene* 104:139–145) and microscopically (Hooper et al., 1990, *J. Biolum. and Chemilum.* 5:123–130).

C. Imaging of Light-Emitting Biodetectors

Light emitting biodetectors may be imaged in a number of ways. Guidelines for such imaging, as well as specific examples, are described below.

1. Photodetector Devices

In one embodiment of the present invention where the signal generated by the biodetector is light, an important aspect will be the selection of a photodetector device with a sensitivity high enough to enable the imaging of faint light. Furthermore, in cases where the biodetector is used in a living subject, the imaging has to be in a reasonable amount of time, preferably less than about thirty (30) minutes.

In cases where it is possible to use light-generating moieties which are extremely bright, and/or to detect light-emitting conjugates localized near the surface of the subject or animal being imaged, a pair of "night-vision" goggles or a standard high-sensitivity video camera, such as a Silicon Intensified Tube (SIT) camera (e.g., Hamamatsu Photonic Systems, Bridgewater, N.J.), may be used. More typically, however, a more sensitive method of light detection is required.

At extremely low light levels, such as those encountered in the practice of the present invention, the photon flux per unit area becomes so low that the scene being imaged no longer appears continuous. Instead, it is represented by individual photons which are both temporally and spatially distinct from one another. Viewed on a monitor, such an image appears as scintillating points of light, each representing a single detected photon.

By accumulating these detected photons in a digital image processor over time, an image can be acquired and constructed. Alternatively, the scintillating points can be enumerated and reported numerically, thus obviating the image reconstruction step and expediting the analysis. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor.

Reduced-Noise Photodetection Devices. The first class constitutes devices which achieve sensitivity by reducing the background noise in the photon detector, as opposed to amplifying the photon signal. Noise is reduced primarily by cooling the detector array. The devices include charge coupled device (CCD) cameras referred to as "backthinned," cooled CCD cameras. In the more sensitive instruments, the cooling is achieved using, for example, liquid nitrogen, which brings the temperature of the CCD array to approximately −120° C. The "backthinned" refers to an ultra-thin backplate that reduces the path length that a photon follows to be detected, thereby increasing the quantum efficiency. A particularly sensitive backthinned cryogenic CCD camera is the "TECH 512," a series 200 camera available from Photometrics, Ltd. (Tucson, Ariz.).

Photon Amplification Devices. A second class of sensitive photodetectors includes devices which amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification.

An exemplary microchannel intensifier-based single-photon detection device suitable for the practice of the invention is the C2400 series, available from Hamamatsu.

Image Processors. Signals generated by photodetector devices which count photons need to be processed by an image processor in order to construct an image which can be, for example, displayed on a monitor or printed on a video printer. Such image processors are typically sold as part of systems which include the sensitive photon-counting cameras described above, and accordingly, are available from the same sources (e.g., Photometrics, Ltd., and Hamamatsu). Image processors from other vendors can also be used, but more effort is generally required to achieve a functional system.

The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP," Adobe Systems, Mountain View, Calif.) and printed.

2. Constructing An Image Of Photon Emission

In cases where, due to an exceptionally bright light-generating moiety and/or localization of light-emitting conjugates near the surface of the subject, a pair of "nightvision" goggles or a high sensitivity video camera was used to obtain an image, the image is simply viewed or displayed on a video monitor. If desired, the signal from a video camera can be diverted through an image processor, which can store individual video frames in memory for analysis or printing, and/or can digitize the images for analysis and printing on a computer.

Alternatively, if a photon counting approach is used, the measurement of photon emission generates an array of numbers, representing the number of photons detected at each pixel location, in the image processor. These numbers are used to generate an image, typically by normalizing the photon counts (either to a fixed, pre-selected value, or to the maximum number detected in any pixel) and converting the normalized number to a brightness (grayscale) or to a color (pseudocolor) that is displayed on a monitor. In a pseudocolor representation, typical color assignments are as follows. Pixels with zero photon counts are assigned black, low counts blue, and increasing counts colors of increasing wavelength, on up to red for the highest photon count values. The location of colors on the monitor represents the distribution of photon emission, and, accordingly, the location of light-emitting conjugates.

In order to provide a frame of reference for the conjugates, a grayscale image of the (still immobilized) subject from which photon emission was measured is typically constructed. Such an image may be constructed, for example, by opening a door to the imaging chamber, or box, in dim room light, and measuring reflected photons (typically for a fraction of the time it takes to measure photon emission). The grayscale image may be constructed either before measuring photon emission, or after.

The image of photon emission is typically superimposed on the grayscale image to produce a composite image of photon emission in relation to the subject.

If it desired to follow the localization and/or the signal from a light-emitting conjugate over time, for example, to record the effects of a treatment on the distribution and/or localization of a selected biocompatible moiety, the measurement of photon emission, or imaging can be repeated at selected time intervals to construct a series of images. The intervals can be as short as picoseconds (in fast gated cameras) or seconds, to days or weeks with integrating cameras.

D. Applications

Specific applications of the biodetectors include the diagnosis of diseases, detection of clinically relevant substances, detection of environmental contaminants, detection of food contaminants. Further, the biodetectors of the invention will find numerous applications in basic research and development.

Diagnosis of Infectious Disease. The biodetectors may be used for the detection of antigens in body fluids, including blood or urine, or tissues and other fluids. Suitable target antigens include, but are not limited to, bacterial pathogens, viral pathogens, fungal pathogens, serum proteins, lymphokines, cytokines, cytotoxins, interferons, β-2 microglobulin, immunoglobulins, peptides, and polypeptides.

Specific diagnostic tests targeting bacterial pathogens may include, but are not limited to, diagnosis of lyme disease, Streptococcus, Salmonella, Tuberculosis, Staphylococcus, Pseudomonas, Helicobactor, Listeria, Shigella, Proteus, Enterococci, Clostridium, Bordatella, Bartonella, Rickettsia, Chlamydia, Spirochetes, as well as products (e.g., toxins) of these and other pathogens. Diagnostic tests targeting viral pathogens may include, but are not limited to, the detection of retroviruses, such as HIV-1, HTLV-1, hepatitis viruses (HBV, HCV, HAV), herpes viruses, including EBV, CMV, herpes simplex I, herpes simplex II, and HHV-6, alphaviruses, including Japanese encephalitis virus, Eastern and Western Encephalitis Virus, rotaviruses, Rhinoviruses, influenza viruses, Pox viruses, all known and yet to be identified human and animal viral pathogens, and unconventional agents such as those associated with Alzheimer's and Crutzfeld-Jacob disease (prions). Targeting fungal pathogens may include, but are not limited to, cryptococcus, histoplasmosis, coccidiodes, and candida.

Detection of Other Clinically Relevant Substances. Applications of the biodetectors may include the detection of clinically relevant substances, such as sugar molecules, fatty acids, or proteins, in body fluids, e.g., blood or urine, or tissue. Targeted antigens may include enzymes indicating the proper function of organs, including lactate dehydrogenase, urea, glucose, and other small molecules, and cytokines. Alpha fetal protein may be targeted for the diagnosis of spinobifida. Certain bacterial species or other microorganisms may be targeted to measure their representation in mixed populations such as gut and vaginal flora. An important diagnostic target will be lymphokines for the diagnosis and prognosis of a range of diseases. With current methods, the profile of lymphokines cannot easily be determined, however, it can be expected that its determination will elucidate a wide array of unknown aspects about the relationship of diseases and disease states. Further, may be applied to the early, perinatal diagnosis of genetic diseases, including cystic fibrosis, sickle cell anemia, Down syndrome, phenylketonuria, ADA deficiency, thallassemias, growth hormone deficiency, predisposition of cancer. In addition, the biodetectors may find application in the real time monitoring of, e.g., glucose levels and drug levels. Finally, biodetectors of the invention may be used in testing for the presence of drugs and/or their metabolites in various drug testing applications.

Agricultural and Veterinary Applications. All above described medical applications may be applied to veterinary medicine.

Detection of Environmental Contaminants. For example, the biodetectors may be used for detection of contaminants in water supply. Selected targets may include, but are not limited to Giardia, Cryptococcus, Legionella, Clostridia toxins, Enterobacter, E. coli, protozoans, heavy metals. Further, representation of certain bacteria in soil populations may be measured by the means of the biodetectors; soil may be screened to track genetically engineered organisms that might have been released into the environment.

Detection of Food Contaminants. The biodetectors may be employed to identify contaminants in food, including, but not limited to, bacteria, such as Salmonella, Coliforms, Staphylococcus, Clostridium, and fungi.

Basic Research and Development. The biodetectors will find numerous applications in basic research and development. Examples include detection system in standard immunoassay, such as Western Blots, ELISA, the determination of lymphokine profiles, the detection of cell culture contamination, including Mycoplasma. Further, the biodetectors will be useful as detection system in expression assays, for the detection of cell surface markers, such as CD4, CD8, adherins.

Abiotic Biodetectors. For certain applications, when antigenicity is an issue (i.e., in vivo) abiotic biodetectors may be desirable. Examples include the in vivo detection and localization of infection, tissue damage and other pathologies. Encapsulation of the biodetector mechanism in generally inert vesicles bilayer or membranes or any other entity that is non-living and will preserve vectoral metabolism (such as liposomes) in such way that contact with ligands results in light will permit the use of this system in vivo.

The following examples illustrate, but in no way are intended to limit the present invention.

VII. EXAMPLES

Material and Methods

Nucleic acid primers (e.g., PCR primers) may be obtained from Operon Technologies, Alameda, Calif. Primer sequences are designed using Oligo software (Rychlik and Rhoads (1989) *Nucleic Acids Res* 17:8543–8551) and unless otherwise indicated, are derived from published sequences available from public sequence databases (e.g., Genbank). DNA sequencing may be carried out on an ABI Prism 310 System (PE Applied Biosystems, Foster City, Calif.). Unless otherwise indicated, all molecular cloning techniques and PCR reactions are carried out using standard methods (Ausubel, et al., 1998, "Enzymatic manipulations of DNA and RNA", in *Current Protocols in Molecular Biology*, pg. 3.0.1–3.19.8; Ausubel, et al., 1998, "The polymerase chain reaction", in *Current Protocols in Molecular Biology*, pg. 15.0.1–15.8.8). Bacteria are transformed using standard electroporation or $CaCl_2$ methods (Ausubel, et al., 1998, "Introduction of plasmid DNA into cells", in *Current Protocols in Molecular Biology*, pg. 1.8.1–1.8.10).

The following examples represent approaches which may be employed to link the signal transduction to the expression of a specific gene.

Example 1

Linking Signal Transduction to the Regulation of a Specific Gene (Approach 1)

The following example illustrates one approach which can be used to link the signal transduction to regulation of a specific gene.

A transposon is constructed to identify promoters that are activated by ligand binding to surface expressed ligand-binding molecules, e.g., antibodies. Promoterless reporter systems have been employed for identifying a variety of regulatory sequences in bacteria. Ronald et al., 1990, *Gene* 90:145–148. The transposon consists of (i) (1) a promoterless operon containing the genes for bioluminescence, (2) a selectable marker (kanamycin resistance gene; Kan), and (3) a negative regulator (the lambda repressor); (ii) an additional selectable marker (chloramphenicol resistance gene; Chl) expressed by the lambda operator; and (iii) a third selectable marker that is constitutively expressed (ampicillin resistance gene; Amp). Bacterial cells expressing the antibody of interest are transformed with the transposon. The conformational change in the transmembrane antibody-fusion protein signals the activation or chemical modification of the transducer which is designed to relay that message to the promoter region of the lux construct. Positive transformants are selected by determination of the acquired Amp resistance. Cells containing the transposon behind promoters that are active in the presence of antigen (including constitutive expression) will be Kan resistant in the presence of antigen, and cells containing a transposon behind promoters that are off in the absence of antigen will be Chl resistant in the absence of antigen. Therefore by passage through a series of growth conditions the desired transformants that appropriately express luciferase in response to antigens will be identified. The promoters can then be characterized and used to construct additional biodetectors.

FIG. 4 depicts a biodetector generated as described in EXAMPLE 1. As shown in FIG. 4A, in the absence of antigen, the fusion protein does not transduce a signal to the promoter which drives expression of the cloned genes encoded by the integrated transposon. Therefore, the phenotype of the proposed *E. coli*, in the absence of antigen, is ampicillin resistant, chloramphenicol resistant, kanamycin sensitive, and not bioluminescent. Ampicillin resistance is constitutively expressed to maintain selection of the integrated transposon.

When, however, the promoter is turned on by binding of the activated transducer, which is activated by ligand binding to the fusion protein, the luciferase operon, the kanamycin resistance gene, and the lambda repressor are expressed. The lambda repressor acts on the lambda operator, thereby shutting down the expression of the chloramphenicol resistance gene. In the presence of antigen the phenotype of the cells is therefore characterized by ampicillin resistance, kanamycin resistance, chloramphenicol sensitivity, and bioluminescence.

Thus, induction and activation of genes as described above permits positive selection for the desired response to antigen. More specifically, only those bacterial cells which integrate the described transposon at a suitable site in the genome survive the selection procedures while nonresponsive bacteria die.

Example 2

Linking Signal Transduction to the Regulation of a Specific Gene (Approach 2)

The following example illustrates a second approach which can be used to link the signal transduction to regulation of a specific gene. It employs a fusion protein composed of an antibody heavy chain and a surface protein known to transduce signals for gene regulation, and a promoter that is affected by this signal placed in front of the reporter operon.

A. Construction of luciferase reporter construct. The promoter region of the *S. typhimurium* phoN gene (Kasahara, et al., 1991, *J. Bacter.* 173:6760–6765) was amplified by PCR using standard methods (Ausubel, F. M., et al., *Current Protocols in Molecular Biology* (John Wiley and Sons, Inc., Media, Pa.) with specific primers (DP1, having the sequence 5' CTG CTG TCT AGA TTA CTT AGC TAC AGG GAG 3' (SEQ ID NO:1), corresponding to bp 5–22 of the sequence having Genbank accession number X63599; and DP2, having the sequence 5' GAC CAA GGA TCC CAT AAA GAC TCA CTC CGG 3' (SEQ ID NO:2), corresponding to bp 532–549 of the sequence having Genbank accession number X63599). The primers were designed with enzyme restriction sites near their 5' ends— DP1 contains an Xba I site, and DP2 contains a Bam HI site. The PCR products were purified using a "QIAquick" PCR purification column (Qiagen Inc., Valencia, Calif.) and cloned into a "pBlueScript II" vector (Stratagene, La Jolla, Calif.) that contains the luxCABDE operon from *P. luminescens*. This plasmid construct is transformed into *E. coli* and screened for bioluminescence under conditions that activate the PhoP/Q signal transduction system. The phoN-lux construct is then permanently introduced into the *E. coli* bacterial genome by Tn5 transposon insertion using standard techniques (Simon R, et al., 1989 *Gene* 80:161–169). The construct preferably contains an antibiotic resistance gene (e.g., ampicillin resistance gene) under the control of a constitutive promoter so that selection of the integrated transposon is possible.

B. Construction of Phage-Antibody Display Library. Messenger RNA is isolated from a number of naive mouse splenic lymphocytes and converted into cDNA using commercially available kits (available from, e.g., Promega Corporation, Madison, Wis.). This pool of cDNA serves as the template for PCR-amplified antibody genes. A first set of primers specific for the variable region of the heavy chain and a second set of primers for the variable region of the light chain have been previously described (Orum, et al. 1993 *Nucleic Acids Res* 21:4491–4498). These are used in separate PCR reactions to generate a large pool of variable region fragments. By a series of PCR reactions the heavy and light chain fragments are connected to a linker that acts as a hinge region and allows the heavy and light chains to form a single chain variable fragment (ScFv) (Orum, et al., 1993, *Nucleic Acids Research* 21(19):4491–4498. Using a commercially available kit for Ab-phage display (Stratagene, La Jolla, Calif.), these DNA fragments are cloned into a phagemid vector and transformed into a bacterial host. Phage particles are rescued with a helper virus and ScFvs are displayed on the surfaces of the phage in the library.

C. Antibody Selection and Screening. Selection of antigen specific antibodies is accomplished by bio-panning methods (Hoogenboom, H. R, 1997 *Trends Biotechnol* 15:62–70). The agent (e.g., bacteria, virus, toxin, or purified protein) is attached to a solid support, such as immunotubes, polystyrene plates, or sepharose columns. The phage library expressing ScFvs is panned over the immobilized antigen, washed, and phage that specifically bind are eluted and amplified. Successive rounds of this selection process increase specificity and affinity.

D. Construction of PhoQ Fusion Protein Expression Cassettes. A vector effective to express and target fusion proteins of PhoQ and selected antibody-fragments PhoQ fusion protein to the cell surface is constructed. The expression cassette in the vector includes, from the 3' end, the following elements: (i) DNA encoding an N-terninal leader sequence, (ii) a cloning site for the insertion of an ScFv DNA, (iii) DNA encoding a membrane anchor (e.g., PAL), and (iv) a fragment comprising the 3' end of the phoQ gene. The 3' end of the phoQ gene (the phoQ gene minus the 5' sensing domain (Miller, 1991, *Mol. Microbiol.* 5:2073–2078)) encodes the active or signal transforming portion of PhoQ, which is capable of activating the transducer PhoP.

DNA encoding the N-terminal leader sequence from the exported bacterial protein pectate lyase, is ligated upstream of a cloning site suitable for accepting a selected ScFv fragment generated as described above. DNA encoding a modified form of *E. coli* cell envelope component PAL (Fuchs, et al., U.S. Pat. No. 5,591,604, issued Jan. 7, 1997) is ligated downstream of the ScFv fragment cloning site. The 3' end of the phoQ gene encoding the signal transforming portion of PhoQ is amplified by PCR using specific primers and inserted downstream of the PAL sequence. The expression cassette is purified and cloned into a vector, containing a selectable antibiotic resistance gene (e.g., Amp), that allows surface expression of the protein (e.g., the pAP1 vector described in Fuchs, et al., 1997, supra).

The antibody variable region genes are amplified by PCR from the DNA isolated from specific phage clones. The amplified PCR fragment are purified and cloned into the cloning site of the PhoQ fusion plasmid constructed as described above. The plasmid is transformed into the phoN-lux *E. coli* and antibiotic resistant colonies are screened for light production in the presence of an antigen specific for the expressed ScFv fragment.

Example 3

Multiple Biodetectors

Construction of Cell-based Sensor Library. The molecular techniques detailed above may be applied to the generation of a library of cell-based sensors. The library is generated essentially as described in Example 2D. A mixture of antibody variable region genes amplified by PCR from either the original lymphocyte cDNAs or from the phagemids are purified and cloned into the cloning site of the PhoQ fusion plasmid constructed as described above. The plasmid is transformed into the phoN-lux *E. coli* and grown on antibiotic-containing media. The resulting transformants comprise a library of *E. coli* which can be screened for response to a selected antigen. Cells which light up for a selected antigen are then selected for use as biodetectors for that particular antigen.

Construction of Ordered Array Format. Individual biodetectors, or biodetectors selected from a library as described above may be arranged into arrays to provide a more convenient screening format. Such ordered arrays are capable of screening for a large number of agents with one sample. Ordered arrays may be arranged on a silicon chip or attached via alginate or similar compounds to a transparent support such as Mylar film. Semi-permeable membranes which overlay the arrays may be used to form "envelopes" into which samples (e.g., blood or urine) may be injected. After a suitable incubation time the envelopes are read in a suitable luminescence reader.

Example 4
Detection of Substances in Solution

The following is an illustrative assay to detect ligands including viral and bacterial antigens in solutions such as whole blood and plasma.

Samples containing the ligand to be detected and quantified are diluted (2 fold serial dilutions) in 96 well plates along with reference standards. The specific biodetector is added to each of the wells as a viable active cell, and analyzed immediately. Bioluminescent signals from the plate are detected using a charge coupled device (CCD camera) or a luminometer in a 96 well format. Relative bioluminescence from the unknown samples are plotted on a standard curve for quantitation.

Example 5
Detection of Substances on Solid Support

The following is an illustrative assay to detect substances on solid supports such as nitrocellulose or nylon membranes, e.g., in Western blot analyses using specific biodetectors.

Following transfer of the proteins to a solid support (PVDF Immobilon membrane, Millipore) using standardized procedures, the membrane is dried and transferred to a dish containing the specific biodetector, as a biologically active cell, in minimal medium or other clear buffer containing nutrients for bacterial metabolism. After 30 minutes incubation at room temperature, the membrane is removed and sealed while still wet in a zip lock or heat sealable plastic bag. Bioluminescent signal from the biodetectors bound to the membrane is detected using a CCD detector, or other light sensitive detection methods. Signals can be quantified using standard image analysis software.

Example 6
Effect of Human Blood on the Light Emission from Bioluminescent Salmonella As demonstrated in the following example, fewer than ten (10) bacterial cells can be detected with an intensified CCD detector.

Two fold serial dilutions of Salmonella, strain LB5000, that had been transformed with a plasmid that conferred constitutive expression of the luciferase operon were plated in duplicate into 96 well plates. Dilutions were made starting with 30 $\mu$l of growth medium alone (left panel; indicated as LB5000) and with 30 $\mu$l of blood (right panel; indicated as LB5000 and 30 $\mu$l blood) to determine the effects of blood as a scattering and absorbing medium on the limits of detection. Each dilution and the numbers of colony forming units (CFU) implied from plating samples from concentrated wells are indicated in FIG. 5. The relative bioluminescence for each well as determined by analysis of the image generated by the CCD detector is shown (FIG. 5). The signal in the more concentrated wells was off scale and the numbers are therefore not linear at higher concentrations.

All references are incorporated in their entirety.

It is claimed:

1. A biodetector for the detection of a selected substance, said biodetector comprising:

a signal converting element, comprising (i) an extracellular ligand-specific binding domain which specifically binds said selected substance, wherein said ligand-specific binding domain comprises an epitope-binding fragment of an antibody, and (ii) an intracellular signal transforming domain of PhoQ, wherein binding of said substance to said epitope-binding fragment of said ligand-specific binding domain activates said intracellular signal transforming domain providing an activated intracellular signal transforming domain;

a transducer, wherein (i) said transducer has an inactive form and an active form which are distinct from each other, and (ii) said activated intracellular signal transforming domain converts said inactive form of said transducer into said active form of said transducer;

a transcription control element comprising the phoN promoter, wherein expression mediated by said transcription control element is activated by said active form of said transducer; and a reporter gene operatively linked to said transcription control element, wherein expression of said reporter gene mediated by said transcription control element causes expression of a reporter gene product that provides a detectable signal, wherein said detectablen signal is detected optically by bioluminescence detection or fluorescence detection.

2. The biodetector of claim 1, wherein said detectable signal is detectable by bioluminescence detection.

3. The biodetector of claim 2, wherein said reporter gene encodes a luciferase.

4. The biodetector of claim 3, wherein said luciferase is encoded by a luc gene.

5. The biodetector of claim 3, wherein said luciferase is encoded by a lux gene.

6. The biodetector of claim 1, wherein said epitope-binding fragment of an antibody is selected from the group consisting of a single chain variable fragment (ScFv), a Fab fragment, a F(ab')$_2$ fragment, an epitope-binding fragment of a polyclonal antibody, an epitope-binding fragment of a monoclonal antibody, an epitope-binding fragment of a humanized antibody, an epitope-binding fragment of a chimeric antibody, and an epitope-binding fragment of an anti-idiotypic antibody.

7. The biodetector of claim 6, wherein said epitope-binding fragment of an antibody comprises a single chain variable fragment (ScFv).

8. The biodetector of claim 1, wherein said biodetector comprises an intact bacterial cell.

9. The biodetector of claim 8, wherein said biodetector comprises a Gram-positive bacterial cell.

10. The biodetector of claim 9, wherein said bacterial cell is selected from the group consisting of Streptococcus, Staphylococcus, Listeria, Clostridium, Bacillus, and Corynebacteria.

11. The biodetector of claim 8, wherein said biodetector comprises a Gram-negative bacterial cell.

12. The biodetector of claim 11, wherein said bacterial cell is selected from the group consisting of Escherichia, Salmonella, Pseudomonas, Helicobacter, Shigella, Proteus, Bordetella, Neisseria, Haemophilus, Bacteriodes, Vibrio, Brucella, Campylobacter, Klebsiella, and Yersinia.

13. A library of biodetectors, comprising
at least about 1000 biodetectors of claim 8, wherein the extracellular ligand-specific binding domain of each of said biodetectors comprises a different antibody fragment,
a reporter gene operatively linked to said transcription control element, wherein expression of said reporter gene mediated by said transcription control element causes expression of a reporter gene product that provides a detectable signal, wherein said detectable signal is detected optically by means selected from the group consisting of bioluminescence detection and fluorescence detection.

14. An ordered array of the library of biodetectors of claim 13.

15. The biodetector of claim 1, wherein said detectable signal is detectable by fluorescence detection.

16. The biodetector of claim 15, wherein said reporter gene encodes a fluorescent protein.

17. The biodetector of claim 8, wherein said bacterial cell comprises a luciferase operon.

18. The biodetector of claim 1, wherein said bioluminescence detection or fluorescence detection is performed using a charge coupled device camera.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer DP1
      corresponding to bp 5-22 of the sequence having
      GenBank Accession Number X63599

<400> SEQUENCE: 1
ctgctgtcta gattacttag ctacagggag                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer DP2
      corresponding to bp 532-549 of the sequence having GenBank
      Accession Number X63599

<400> SEQUENCE: 2
gaccaaggat cccataaaga ctcactccgg                                    30
```